United States Patent
Hara et al.

(10) Patent No.: US 12,398,411 B2
(45) Date of Patent: Aug. 26, 2025

(54) METHOD FOR PRODUCING SELENONEINE

(71) Applicant: KIKKOMAN CORPORATION, Noda (JP)

(72) Inventors: Seiichi Hara, Noda (JP); Keiichi Ichikawa, Noda (JP)

(73) Assignee: KIKKOMAN CORPORATION, Noda (JP)

( * ) Notice: Subject to any disclaimer, the term of this patent is extended or adjusted under 35 U.S.C. 154(b) by 1112 days.

(21) Appl. No.: 17/251,975

(22) PCT Filed: Jun. 14, 2019

(86) PCT No.: PCT/JP2019/023590
§ 371 (c)(1),
(2) Date: Jul. 12, 2021

(87) PCT Pub. No.: WO2019/240243
PCT Pub. Date: Dec. 19, 2019

(65) Prior Publication Data
US 2023/0159968 A1  May 25, 2023

(30) Foreign Application Priority Data
Jun. 15, 2018 (JP) ................................ 2018-114919

(51) Int. Cl.
| | |
|---|---|
| C12P 17/10 | (2006.01) |
| C12N 9/10 | (2006.01) |
| C12N 15/52 | (2006.01) |
| C12N 15/70 | (2006.01) |
| C12N 15/80 | (2006.01) |
| C12P 9/00 | (2006.01) |
| C12P 13/04 | (2006.01) |

(52) U.S. Cl.
CPC ............ *C12P 17/10* (2013.01); *C12N 9/1025* (2013.01); *C12N 9/1085* (2013.01); *C12N 15/52* (2013.01); *C12N 15/70* (2013.01); *C12N 15/80* (2013.01); *C12P 9/00* (2013.01); *C12P 13/04* (2013.01); *C12Y 203/0103* (2013.01); *C12Y 205/01047* (2013.01)

(58) Field of Classification Search
None
See application file for complete search history.

(56) References Cited

U.S. PATENT DOCUMENTS

| | | | | |
|---|---|---|---|---|
| 11,028,400 | B2 * | 6/2021 | Ichikawa ................ | C12N 9/88 |
| 11,629,341 | B2 * | 4/2023 | Ichikawa ............ | C12N 9/0071 |
| | | | | 435/121 |
| 2011/0178018 | A1 | 7/2011 | Yamashita et al. | |
| 2015/0175981 | A1 | 6/2015 | Olsen | |
| 2017/0356017 | A1 | 12/2017 | Hara et al. | |
| 2018/0237815 | A1 | 8/2018 | Ichikawa et al. | |

FOREIGN PATENT DOCUMENTS

| | | | |
|---|---|---|---|
| CN | 108138206 | 6/2018 | |
| JP | 2017046594 | 3/2017 | |
| WO | WO-2017026173 A1 * | 2/2017 | ............... C12N 1/14 |
| WO | 2017/188355 | 2/2019 | |

OTHER PUBLICATIONS

Chen Y et al. FEMS Yeast Res. Aug. 2012; 12(5):598-607 (Year: 2012).*
Pluskal T et al. PLoS One. May 14, 2014;9(5):e97774 (Year: 2014).*
De Vries et al. Genome Biol. Feb. 14, 2017;18(1):28 (Year: 2017).*
Rosano GL et al. Front Microbiol. Apr. 17, 2014;5:172 (Year: 2014).*
Notification concerning transmittal of international preliminary report on patentability (Form PCT/IB/326).
International preliminary report on patentability (Form PCT/IB/373).
Notification of transmittal of translation of the international preliminary report on patentability (Form PCT/IB/338).
Translation of International preliminary report on patentability (Form PCT/IB/373).
Office Action from JPO (Japanese version and English Machine Translation)—Patent Application No. JP2020-525669 Issue date: Sep. 13, 2022.
Office Action from JPO—Patent Application No. JP2020-525669 Issue date: Dec. 6, 2022.
International Search Report of corresponding PCT application (Japanese version and English Version) (PCT/JP2019/023590).
Jain, S. at al., "Selenate sensitivity of a laeA mutant is restored by overexpression of the bZIP protein MetR in Aspergillus fumigatus.", Fungal Genetics and Biology, Available online May 2018, vol. 117, p. 110.
Amich, J. et al., "Regulation of sulphur assimilation is essential for virulence and affects iron homeostasis of the human pathogenic mould Aspergillus fumigatus.", PLOS pathogens, 2013, vol. 9, No. 8, e1003573, p. 124.
Pluska et al., "Genetic and Metabolomic Dissection of the Ergothioneine and Selenoneine Biosynthetic Pathway in the Fission Yeast, S. pombe, and Construction of an Overproduction System" PLoS One May 14, 2014; 9(5):e97774.

(Continued)

*Primary Examiner* — Nancy J Leith
*Assistant Examiner* — Douglas Charles Ryan
(74) *Attorney, Agent, or Firm* — JMB Davis Ben-David

(57) ABSTRACT

The purpose of the present invention is to provide a method for producing selenoneine that allows production of selenoneine at higher yields, even if an inorganic selenium compound is used as a selenium compound. This purpose can be achieved by a method for producing selenoneine, comprising the step of applying histidine and a selenium compound to a transformant to obtain selenoneine, wherein the transformant has at least one gene selected from the group consisting of a SatA gene, a CysB gene and a MetR gene, and an EgtA gene inserted therein and can overexpress the inserted genes.

6 Claims, 3 Drawing Sheets
Specification includes a Sequence Listing.

(56) References Cited

OTHER PUBLICATIONS

Extended European Search Report of corresponding EP patent application No. 19818552.2, Apr. 20, 2022.
Kelly et al., "Multiple copies of the amdS gene of Aspergillus nidulans cause titration of trans acting regulatory proteins" Curr. Genetics 12:21-31, 1987.
Liu et al., "Genome-scale analysis of the high-efficient protein secretion system of Aspergillus oryzae," BMC ystems Biology 8:73, 2014.
Office Action from CNIPA (Chinese version and English Translation) Patent Application No. CN201980039798.1 Issue date: Jun. 7, 2023.

* cited by examiner

[FIG.1A]
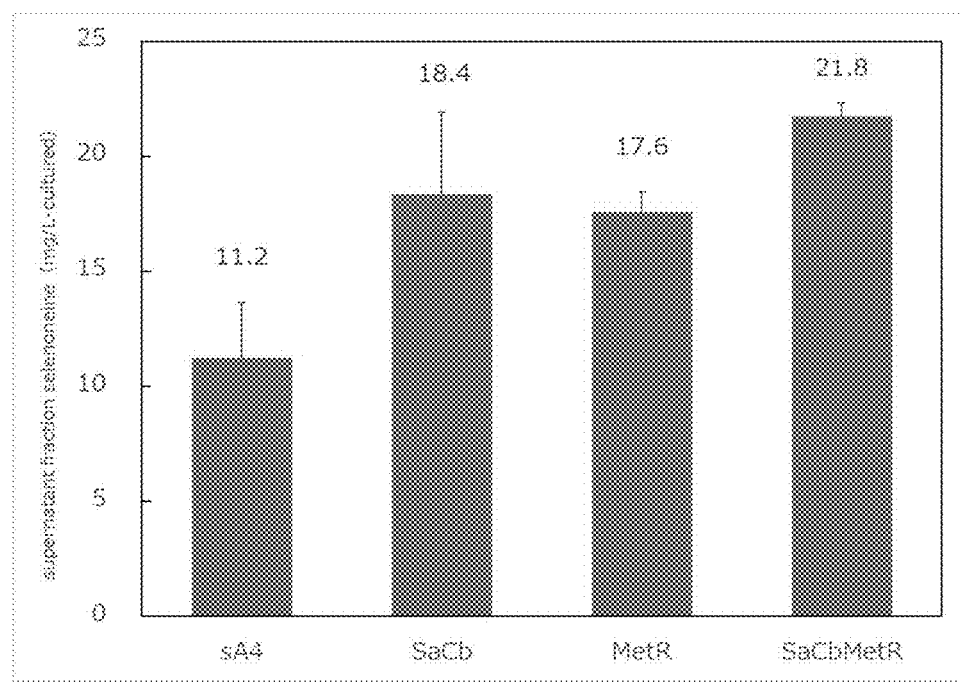
[FIG.1B]
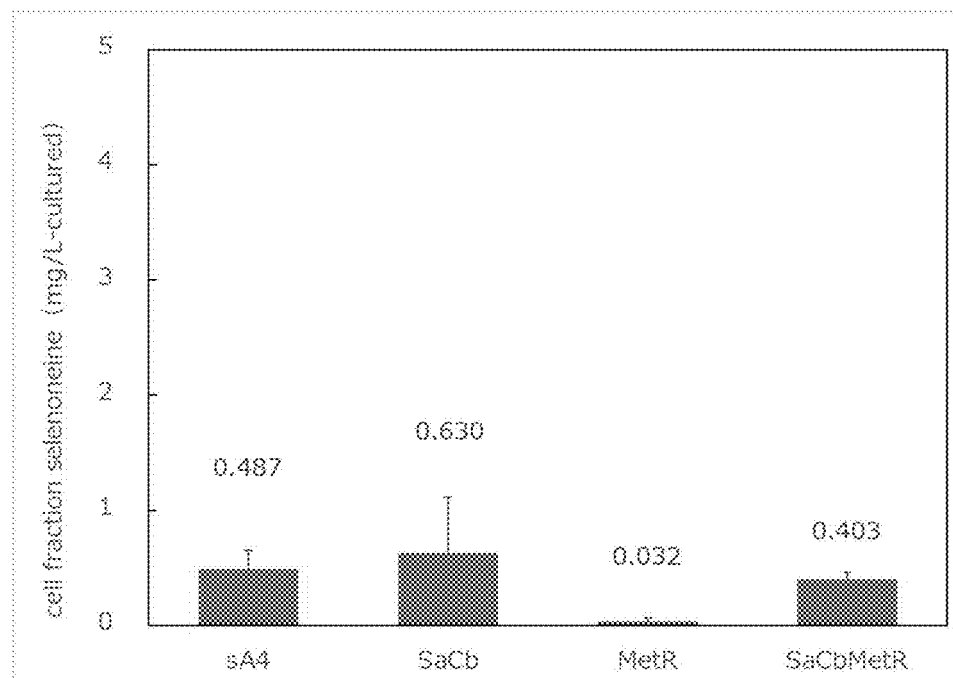

[FIG.2]
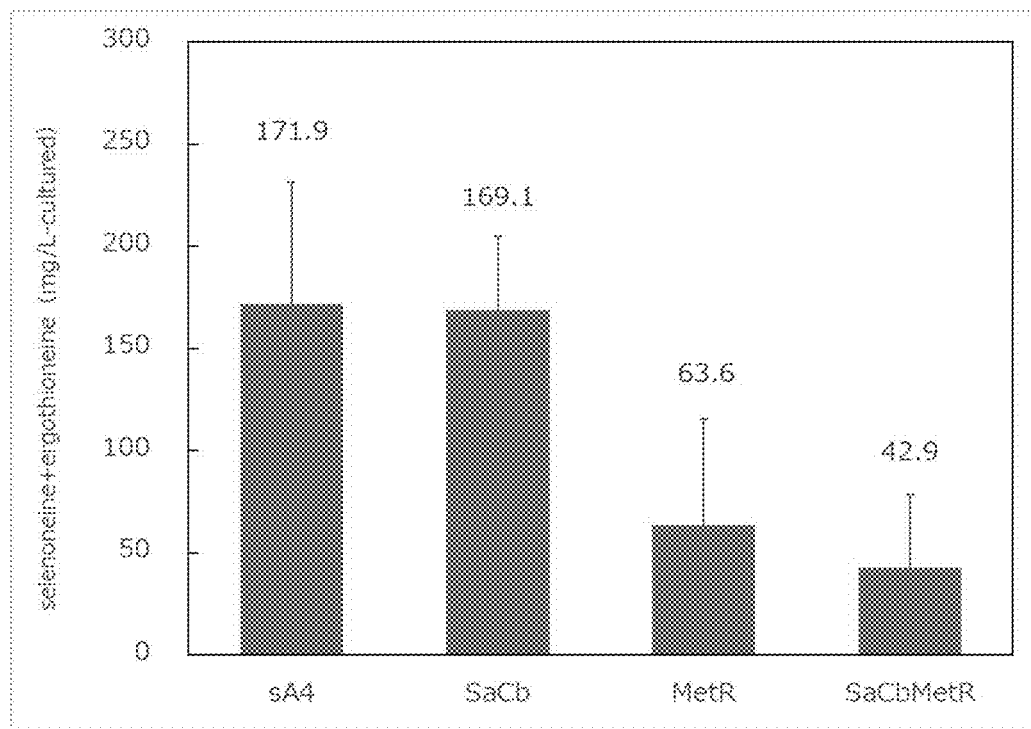
[FIG.3]
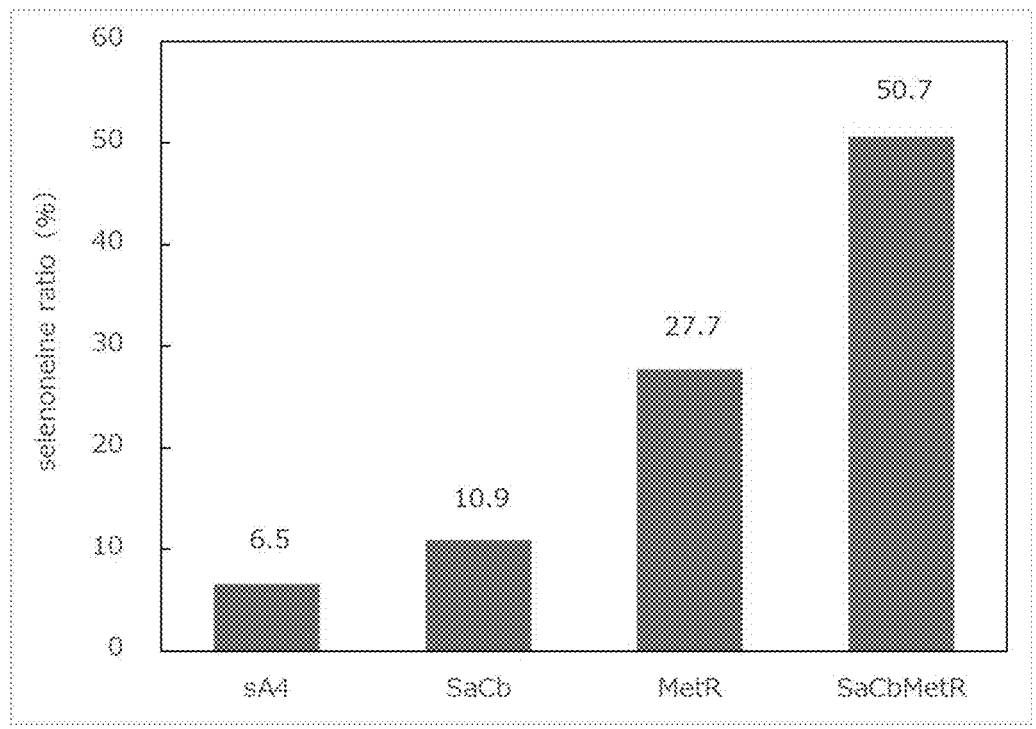

[FIG.4]
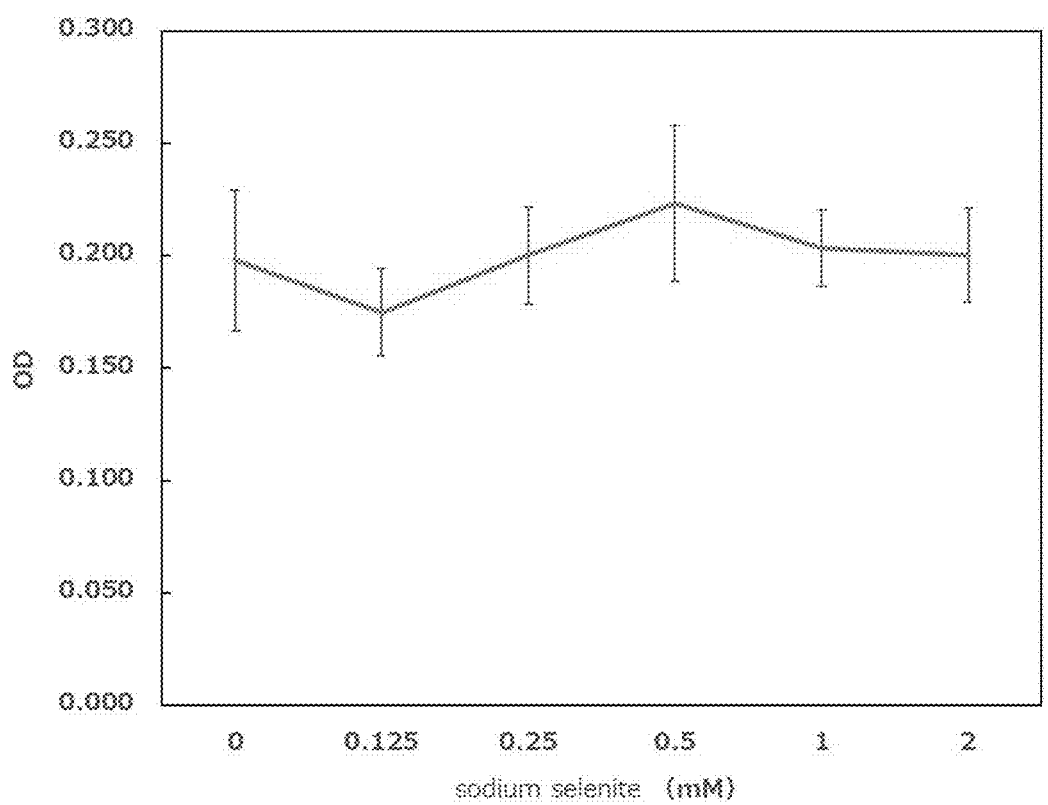

SEQUENCE LISTING

<160> NUMBER OF SEQ ID NOS: 59

<210> SEQ ID NO 1
<211> LENGTH: 2925
<212> TYPE: DNA
<213> ORGANISM: Aspergillus sojae

<400> SEQUENCE: 1

```
atgtcacctt tggctctctc tcctaagacc gttgacattg tcaacatctt tcagaatgat      60
gtggagttct ccctcgtaaa tgagatccat aagggtatta gtcctcccgc tggcgttagg     120
aagtcaatgc caacgatgct tctttacgat gccaatggcc tcaagctttt tgagaacatc     180
acctatgtga aggagtatta tctaacaaat gcggaaattg aggtcttgga gacaaattcc     240
aggaggatag ttgaacggat tccagacaat gcgcaactgc ttgaattagg tagcgggtgc     300
gtcatccttc caaatcaaat cgtaaccttt caggctgcgt agcgtatcat taccgttctc     360
cggttttaac cgccttttag gaatcttcgg aaaattgaga ttctgctacg ggagtttgag     420
cgcgtgggaa agcgcgtgga ttattatgcc ctggacctgt ctctatcaga actgcagcgc     480
acattcgcag aggtgtccat tgatgattac acacacgttg gcctccatgg tctccatgga     540
acctacgatg atgccgtcac ttggcttaac agccccgaaa acaggaagcg gcccacggtg     600
atcatgtcta tgggttcctc tttagggaac tttgaccgtc ccggcgcagc aaagtttctc     660
tcgcagtatg ctagccttct tggtccatcc gatatgatga tcattggtct ggatggctgc     720
aaggacccgg gcaaagtata cagggcatac aatgattcag aaggtgttac acggcagttc     780
tacgagaacg gactagtgca tgcaaatgtt gttcttggat acgaagcctt caaatctgat     840
gagtgggaag tagtgactga ctacgatacc gtggagggac gacactgggc agcctactca     900
cccaagaagg acgtcactat caacggggtc cttcttaaga agggtgagaa acttttcttt     960
gaagaggcgt acaagtacgg accagaggaa cgcgatcaac tgtggcgtga tgccaagtta    1020
attcagtcta cggaaatggg caatgggtct gacgattacc gtgagtagca aatggctgcc    1080
tcatttcaat agacgtgtat gctgactctg gcttttcgca aaatagatct ccatcttctg    1140
acatcggcta ccctcaacct ccccacgtct ccctctcaat atgcagctca tcctataccc    1200
agctttgaag aatggcagtc cctgtggaca gcatgggata tgctacaaa ggctatggtc    1260
cctcgcgagg agcttctgtc aaagccgatc aagctacgga actctttgat cttctatctg    1320
ggacacattc ctacattctt gggttagtct acatggctta ctattcccaa cacatagctt    1380
gatgctaatt atgcaaacag acatccatct gacccgagcc ctgcgcggaa aattaacaga    1440
gccaaagtct tataaactaa ttttcgaacg tgggattgat cctgatgtag atgaccccga    1500
gaagtgccac tcccatagcg agatcccaga cgagtggcca gctcttgatg acattctaga    1560
ctaccaagag cgagtcagaa gcagagttag atccatctac caaatcgagg gccttgcaga    1620
gaacagaatc ctgggtgagg cgcttttggat tggatttgag cacgaagtga tgcacctcga    1680
gacattcctg tacatgttga tccagagcga aaggatactt ccccgcccg ccactgagcg    1740
gccggacttc aaaaaactgt atcaagaagc tcggagaagc atgaaagcaa atgagtggtt    1800
ctctgttcct gaacagacac ttactattgg ccttgatggt gctgatacca acgacgtacc    1860
cccaacgacc tatgggtggg acaatgagaa acctgcgaga acagtcacgg ttccagcatt    1920
tgaggcgcag ggcaggccca tcaccaatgg tgagtacgcc aagtacttgc aagcgaatca    1980
gtcgcgcaga aggccagcat catgggtcct gacccattcg gatgaagact acgccatacc    2040
tatgcggtc aacggaagca gtgtcggggc tacgcaggac tttatgtcca actttgctgt    2100
ccgtacggtc ttcggcccag ttccacttga atttgctcag gactggcctg tgatggcgtc    2160
atatgatgaa ttagctgaat acgccgaatg ggtgggttgc aggatcccaa ccttcgaaga    2220
gacaaggagt atctatctgc actcagcgct attgaaggaa agaggtggcg tgaatcataa    2280
```

| | |
|---|---|
| tggggagccc aacggccata ggttagtgca gcctcattat aacaccacat tcgggattaa | 2340 |
| gctgagctaa cggctgtcag tttgaacggc gatctgaatg gggtgaatgg aaatggttac | 2400 |
| tcgaagatca acccaggcaa acctcgtaag ccggatcacc agcctgtaca atatccttcc | 2460 |
| cgagacgccc tgccagtgtt ccttgatctg cacggtctca acgtcgggtt caagcactgg | 2520 |
| caccccaccc cagttatcca gaacggcgat cgactcgccg gtcagggtga actgggaggc | 2580 |
| gcatgggagt ggactagcac gccattagcg ccacacgatg gctttaaagc catggagatc | 2640 |
| tacccgggat acacctgtaa gtaccagtcc cgttatcggg taccctctaa aagtctatca | 2700 |
| ttacatacta attccgcaca gccgatttct tcgacggtaa acataatatc atcctgggtg | 2760 |
| gttcttgggc tactcatccc cgcgtcgctg ggcgtaccac tttgtaagtt taccggtata | 2820 |
| gaactcgggg cactataaga tgctgacatc acctctagcg tcaattggta ccagcacaac | 2880 |
| tatccttaca cctgggcagg agcacgcctg gtgcgggatc tttag | 2925 |

<210> SEQ ID NO 2
<211> LENGTH: 1572
<212> TYPE: DNA
<213> ORGANISM: Aspergillus sojae

<400> SEQUENCE: 2

| | |
|---|---|
| atgggatcta tatacggcgt ggcgcgctca gcgcggagtc tctcagctct gcttagacat | 60 |
| gaaagcgtct cgactcggaa tcgattagca gcagtatgct cgccaacgca atacgcaacg | 120 |
| gcccggaggt cattacacag cggtcgtcca cggaagtccc agtccgccgc cgcaagtaac | 180 |
| aactcatcca atcccgccct atcatttcct tgtcttgacg cccaagatgc gaagtccgct | 240 |
| cttctctccg cacggtctat cgagtcaggc cccgagccgt catacacaac cggccaccat | 300 |
| gaacagttcc gctgcgaaga cccattgctg cttgactggg gtggtgtcct gcccgaattc | 360 |
| gatatcgcat acgaaacatg gggccaattg aacgctgaca gagcaacgc tatcctacta | 420 |
| cacaccggtc tctcggcctc gagtcacgcc catagcaccg aagccaattc caaaccggga | 480 |
| tggtgggaga aattcatcgg ccccggcaaa ccattagata caaacaagca cttcgtcatc | 540 |
| tgtacgaatg ttatcggagg ctgctacggc agcaccgggc cctcgtccat cgaccccctcc | 600 |
| gacggaaaga gatacgccac ccgattcccc atcctgacga tagacgacat ggtgcgcgca | 660 |
| caattccgtc tcttggactc gctgggcatc cagaagctgt acgcctccgt cggctccagc | 720 |
| atgggcggca tgcagagtct cgccgccgga gtgctcttcc ccgagcgcgt cgaaaagatc | 780 |
| gtcagtatca gcggctgcgc ccgaagccac ccatacagca tcgccatgcg acacacgcag | 840 |
| cgccaggtcc tcatgatgga ccccaaatgg gcccgcgggt tctactacga ctccatcccg | 900 |
| ccccattcgg gcatgaagct cgcgcgtgaa atcgccacag ttacctacag aagtggaccc | 960 |
| gaatgggaga agcggtttgg ccgcaagcgt gcagaccca gcaagcagcc tgcattgtgc | 1020 |
| cccgatttcc ttattgagac gtacctcgat cacgcgggcg agaagttctg tctggaatac | 1080 |
| gacccaaaca gtctgctgta tgtctcgaag gccatggact tgtttgatct gggacaggca | 1140 |
| cagcaaacgg agacgaagaa gagacgggcc gagtacgaag ctaatatcgc ggagggaggc | 1200 |
| aagactgttg acgctagcaa tattgcctgc agcctcacgc tcccagagaa gccgtacgaa | 1260 |
| gagcagccgt ctgtgaccgc gtctacgccc gccatggacc agtccgtcac tggaggtgcg | 1320 |
| gaagcgccgc cacaagatct cgtcgctgga ttggcgcctt tgaagaacca tcccgttctg | 1380 |
| gtcatgggtg ttgccagcga tattctcttc cctgcttggc agcagcttga gattgcagag | 1440 |
| acgcttcggg ctggtgggaa cgagaaggtc cagcacattg aacttggtga ggacgtatcg | 1500 |

```
atgttcggac acgatacgtt cctgcttgac ttgaagaaca ttggtggtgc agtagagaaa    1560
ttcttgcgct ga                                                        1572

<210> SEQ ID NO 3
<211> LENGTH: 1183
<212> TYPE: DNA
<213> ORGANISM: Aspergillus sojae

<400> SEQUENCE: 3
atgttccgac aaagtattcg gcgcttcggc accactgcgc tccgcgcagc agaaggatcg      60
accgcctata gcgtccgggt gtcgcaagct cagggctacg ttaacggtct tacagaaggt     120
acgctaagaa gacgaaaata aaagttagct acacgaacaa tggcttctga cagtttgtca     180
ttaagcaatt ggaaacacac cacttatccg attgaagcgt ctctccgaag agactggctg     240
caacatcctc ggtaaagccg agttccagaa ccccggaggc agtgtgaagg accgtgcagc     300
attgttcgtc gtcaaggatg ccgaggagaa gggacttttg aagcctggtg gtacagtggt     360
tgagggaaca gctggtaaca ctggaattgg gttggcgcac gtgtgtaggt caaagggcta     420
caagcttgtc atctacatgc ccaacacgca gtcccagggt aagattgact tgttgcggct     480
gttgggagcg gaggtctacc ctgtaccggc cgtcgccttc gacaacccgc agaactacaa     540
ccaccaggca aggagacatg ccgaatccct ggataacgcc gtatggacga accagttcga     600
caacactgcc aatcgccagg cccacattga gatgaccggg ccggaaatct gggcccagac     660
tggcggacag gtcgatgctt tcacttgtgc tactggaacc ggaggaacat ggccggaat      720 taccccgctat ctgaagaccg cttccgacgg ccgggtgaag tgcttccttg ccgacccccc     780
gggcagtgtc ctgcacagct acatccgag cggcggaaac ctaatcgagc gctcggaag      840 cagcatcacg gagggtattg gtcagggccg cgtcacggac aacctccagc ccgacattga     900
tcttttggat gggtctctga acattagcga tgagaagtcg atcgagatgg tctaccgctg     960
tctcgatgag gaaggtctct atcttggagc tagctctgcg ctcaacgtcg ttgcggccaa    1020
ggaagttgcc gaaaagctcg gtaagggtaa gaccgtcgtc accattctgt gtgatggcgc    1080
ctaccgctat gccgaccgtc tgttctcgaa cacctggctc cagagcaagg gtctgagaac    1140
cgctatccct aagcacttgg agaagtacat cgtgctcccc tga                     1183

<210> SEQ ID NO 4
<211> LENGTH: 1561
<212> TYPE: DNA
<213> ORGANISM: Aspergillus sojae

<400> SEQUENCE: 4
atgtcagatg agcacatcgc tcgtcagaca gcgtcaagcc tcgataggct tgagaatttc      60
aacttcttac tctcccgaca cgatcctgcc ctggcaaaga gtcgacatta ctctttcgac     120
gcagacgcgg ccggcttggc tccttttcaa aacctgagca tggattacga ccagactgag     180
ggaatgggcg gtatttccgt cagttcctac gatagcattg aggatgaacg gaacccgatc     240
gatgtgagag ggtatcccta tcatggtaag tctgagcttt tatgactctc aacgttgcat     300
tgtttgcgcc atcttctcga tccctggttc gtgtctcaat tttatggcct ttgcggcatt     360
aggtggaaat ggtagagcta ttgctgaggc gcactcggat cgtggccaaa gctgatctcg     420
ttcgtctcca tctaaatatc tcctttccct ttttccgggg aaaagcttct tcttgtttgt     480
tgtgccatta gtttgtttgc aattgttaat cgtggctgtc attgttggcg ttgctgtcca     540
```

-continued

```
actcttatcg ctcgtggatc actccatact ttattgccca caacctgtta aagtcaagat    600
ttaactttgg gctcatgtat gttttgcttc atctatctcc ctattgtttt tgcctatttt    660
ttctcttttc ttttttttaag ttgccgattt tcttataccc ctttggttgt attctcatct   720
gcacccgcat gcctggttga tcacggagac gagcacgcaa tccatcacac caatgacaac    780
gtcggtaacc ttgtcgttgg tgttgccgga cccttagcca cgcatctccc tctgttcatc    840
taaagctccc caccaagggt cttatgtccc ctttggagct ttccttgtgt gataacactt    900
gctccttctt tctgtcttta tcaccttgct tgatctatgt ctgcagtgtt gctgtcctag    960
attctgctca ttccgttact tacatctatt cccagcagct gataaacaca tcaactactc   1020
ccttcccgac caaatgatct catatccagc tcacccgatc taccctccaa tctcttatgg   1080
acctgatgat ctgggtcatg ccccgggggc tctgactccc tcggacgttt catcgtccat   1140 atcaccccg aatggtcaac tcggccacac caagtacagc acgcagatcc ctggtgatca    1200
cctcgcttct gcactttcgc aagaagagca tgttcgtcgt gctgccgaag aagaccggcg   1260
gcggcgaaac accgcggcta gcgcccggtt tcgcatgaaa aagaagcagc gtgaacagac   1320
gctggaacgg acggtgcgag agactactga gaagaacgct actctcgagg cccgcgtagc   1380
ccagctggag atggaaaatc gatggttgaa gaatctcttg actgagaaac acgaatcgac   1440
gagtagtcgc atgccgcccc caccggaaga cagcacagcc ttgaaccaaa aaggcaacag   1500
tggcggaagc ggccaaaaac acatccagcc aaaaaagaag ggtgtgggca ccgataacta   1560
g                                                                   1561
```

<210> SEQ ID NO 5
<211> LENGTH: 845
<212> TYPE: PRT
<213> ORGANISM: Aspergillus sojae

<400> SEQUENCE: 5

```
Met Ser Pro Leu Ala Leu Ser Pro Lys Thr Val Asp Ile Val Asn Ile
1               5                   10                  15

Phe Gln Asn Asp Val Glu Phe Ser Leu Val Asn Glu Ile His Lys Gly
            20                  25                  30

Ile Ser Pro Pro Ala Gly Val Arg Lys Ser Met Pro Thr Met Leu Leu
        35                  40                  45

Tyr Asp Ala Asn Gly Leu Lys Leu Phe Glu Asn Ile Thr Tyr Val Lys
    50                  55                  60

Glu Tyr Tyr Leu Thr Asn Ala Glu Ile Glu Val Leu Glu Thr Asn Ser
65                  70                  75                  80

Arg Arg Ile Val Glu Arg Ile Pro Asp Asn Ala Gln Leu Leu Glu Leu
                85                  90                  95

Gly Ser Gly Asn Leu Arg Lys Ile Glu Ile Leu Leu Arg Glu Phe Glu
            100                 105                 110

Arg Val Gly Lys Arg Val Asp Tyr Tyr Ala Leu Asp Leu Ser Leu Ser
        115                 120                 125

Glu Leu Gln Arg Thr Phe Ala Glu Val Ser Ile Asp Asp Tyr Thr His
    130                 135                 140

Val Gly Leu His Gly Leu His Gly Thr Tyr Asp Asp Ala Val Thr Trp
145                 150                 155                 160

Leu Asn Ser Pro Glu Asn Arg Lys Arg Pro Thr Val Ile Met Ser Met
                165                 170                 175

Gly Ser Ser Leu Gly Asn Phe Asp Arg Pro Gly Ala Ala Lys Phe Leu
            180                 185                 190
```

```
Ser Gln Tyr Ala Ser Leu Leu Gly Pro Ser Asp Met Met Ile Ile Gly
        195                 200                 205

Leu Asp Gly Cys Lys Asp Pro Gly Lys Val Tyr Arg Ala Tyr Asn Asp
    210                 215                 220

Ser Glu Gly Val Thr Arg Gln Phe Tyr Glu Asn Gly Leu Val His Ala
225                 230                 235                 240

Asn Val Val Leu Gly Tyr Glu Ala Phe Lys Ser Asp Glu Trp Glu Val
                245                 250                 255

Val Thr Asp Tyr Asp Thr Val Glu Gly Arg His Trp Ala Ala Tyr Ser
            260                 265                 270

Pro Lys Lys Asp Val Thr Ile Asn Gly Val Leu Leu Lys Lys Gly Glu
        275                 280                 285

Lys Leu Phe Phe Glu Glu Ala Tyr Lys Tyr Gly Pro Glu Glu Arg Asp
    290                 295                 300

Gln Leu Trp Arg Asp Ala Lys Leu Ile Gln Ser Thr Glu Met Gly Asn
305                 310                 315                 320

Gly Ser Asp Asp Tyr His Leu His Leu Leu Thr Ser Ala Thr Leu Asn
                325                 330                 335

Leu Pro Thr Ser Pro Ser Gln Tyr Ala Ala His Pro Ile Pro Ser Phe
            340                 345                 350

Glu Glu Trp Gln Ser Leu Trp Thr Ala Trp Asp Asn Ala Thr Lys Ala
        355                 360                 365

Met Val Pro Arg Glu Glu Leu Leu Ser Lys Pro Ile Lys Leu Arg Asn
    370                 375                 380

Ser Leu Ile Phe Tyr Leu Gly His Ile Pro Thr Phe Leu Asp Ile His
385                 390                 395                 400

Leu Thr Arg Ala Leu Arg Gly Lys Leu Thr Glu Pro Lys Ser Tyr Lys
                405                 410                 415

Leu Ile Phe Glu Arg Gly Ile Asp Pro Asp Val Asp Pro Glu Lys
            420                 425                 430

Cys His Ser His Ser Glu Ile Pro Asp Glu Trp Pro Ala Leu Asp Asp
        435                 440                 445

Ile Leu Asp Tyr Gln Glu Arg Val Arg Ser Arg Val Arg Ser Ile Tyr
    450                 455                 460

Gln Ile Glu Gly Leu Ala Glu Asn Arg Ile Leu Gly Glu Ala Leu Trp
465                 470                 475                 480

Ile Gly Phe Glu His Glu Val Met His Leu Glu Thr Phe Leu Tyr Met
                485                 490                 495

Leu Ile Gln Ser Glu Arg Ile Leu Pro Pro Ala Thr Glu Arg Pro
            500                 505                 510

Asp Phe Lys Lys Leu Tyr Gln Glu Ala Arg Arg Ser Met Lys Ala Asn
        515                 520                 525

Glu Trp Phe Ser Val Pro Glu Gln Thr Leu Thr Ile Gly Leu Asp Gly
    530                 535                 540

Ala Asp Thr Asn Asp Val Pro Pro Thr Thr Tyr Gly Trp Asp Asn Glu
545                 550                 555                 560

Lys Pro Ala Arg Thr Val Thr Val Pro Ala Phe Glu Ala Gln Gly Arg
                565                 570                 575

Pro Ile Thr Asn Gly Glu Tyr Ala Lys Tyr Leu Gln Ala Asn Gln Ser
            580                 585                 590

Arg Arg Arg Pro Ala Ser Trp Val Leu Thr His Ser Asp Glu Asp Tyr
        595                 600                 605
```

```
Ala Ile Pro Met Ala Val Asn Gly Ser Ser Val Gly Ala Thr Gln Asp
    610                 615                 620

Phe Met Ser Asn Phe Ala Val Arg Thr Val Phe Gly Pro Val Pro Leu
625                 630                 635                 640

Glu Phe Ala Gln Asp Trp Pro Val Met Ala Ser Tyr Asp Glu Leu Ala
                645                 650                 655

Glu Tyr Ala Glu Trp Val Gly Cys Arg Ile Pro Thr Phe Glu Glu Thr
            660                 665                 670

Arg Ser Ile Tyr Leu His Ser Ala Leu Leu Lys Glu Arg Gly Gly Val
        675                 680                 685

Asn His Asn Gly Glu Pro Asn Gly His Ser Leu Asn Gly Asp Leu Asn
    690                 695                 700

Gly Val Asn Gly Asn Gly Tyr Ser Lys Ile Asn Pro Gly Lys Pro Arg
705                 710                 715                 720

Lys Pro Asp His Gln Pro Val Gln Tyr Pro Ser Arg Asp Ala Leu Pro
                725                 730                 735

Val Phe Leu Asp Leu His Gly Leu Asn Val Gly Phe Lys His Trp His
            740                 745                 750

Pro Thr Pro Val Ile Gln Asn Gly Asp Arg Leu Ala Gly Gln Gly Glu
        755                 760                 765

Leu Gly Gly Ala Trp Glu Trp Thr Ser Thr Pro Leu Ala Pro His Asp
770                 775                 780

Gly Phe Lys Ala Met Glu Ile Tyr Pro Gly Tyr Thr Ser Asp Phe Phe
785                 790                 795                 800

Asp Gly Lys His Asn Ile Ile Leu Gly Gly Ser Trp Ala Thr His Pro
                805                 810                 815

Arg Val Ala Gly Arg Thr Thr Phe Val Asn Trp Tyr Gln His Asn Tyr
            820                 825                 830

Pro Tyr Thr Trp Ala Gly Ala Arg Leu Val Arg Asp Leu
        835                 840                 845

<210> SEQ ID NO 6
<211> LENGTH: 523
<212> TYPE: PRT
<213> ORGANISM: Aspergillus sojae

<400> SEQUENCE: 6

Met Gly Ser Ile Tyr Gly Val Ala Arg Ser Ala Arg Ser Leu Ser Ala
1               5                   10                  15

Leu Leu Arg His Glu Ser Val Ser Thr Arg Asn Arg Leu Ala Ala Val
            20                  25                  30

Cys Ser Pro Thr Gln Tyr Ala Thr Ala Arg Arg Ser Leu His Ser Gly
        35                  40                  45

Arg Pro Arg Lys Ser Gln Ser Ala Ala Ala Ser Asn Asn Ser Ser Asn
    50                  55                  60

Pro Ala Leu Ser Phe Pro Cys Leu Asp Ala Gln Asp Ala Lys Ser Ala
65                  70                  75                  80

Leu Leu Ser Ala Arg Ser Ile Glu Ser Gly Pro Glu Pro Ser Tyr Thr
                85                  90                  95

Thr Gly His His Glu Gln Phe Arg Cys Glu Asp Pro Leu Leu Leu Asp
            100                 105                 110

Trp Gly Gly Val Leu Pro Glu Phe Asp Ile Ala Tyr Glu Thr Trp Gly
        115                 120                 125

Gln Leu Asn Ala Asp Lys Ser Asn Ala Ile Leu Leu His Thr Gly Leu
    130                 135                 140
```

Ser Ala Ser Ser His Ala His Ser Thr Glu Ala Asn Ser Lys Pro Gly
145                 150                 155                 160

Trp Trp Glu Lys Phe Ile Gly Pro Gly Lys Pro Leu Asp Thr Asn Lys
            165                 170                 175

His Phe Val Ile Cys Thr Asn Val Ile Gly Gly Cys Tyr Gly Ser Thr
            180                 185                 190

Gly Pro Ser Ser Ile Asp Pro Ser Asp Gly Lys Arg Tyr Ala Thr Arg
            195                 200                 205

Phe Pro Ile Leu Thr Ile Asp Asp Met Val Arg Ala Gln Phe Arg Leu
210                 215                 220

Leu Asp Ser Leu Gly Ile Gln Lys Leu Tyr Ala Ser Val Gly Ser Ser
225                 230                 235                 240

Met Gly Gly Met Gln Ser Leu Ala Ala Gly Val Leu Phe Pro Glu Arg
                245                 250                 255

Val Glu Lys Ile Val Ser Ile Ser Gly Cys Ala Arg Ser His Pro Tyr
            260                 265                 270

Ser Ile Ala Met Arg His Thr Gln Arg Gln Val Leu Met Met Asp Pro
            275                 280                 285

Lys Trp Ala Arg Gly Phe Tyr Tyr Asp Ser Ile Pro Pro His Ser Gly
290                 295                 300

Met Lys Leu Ala Arg Glu Ile Ala Thr Val Thr Tyr Arg Ser Gly Pro
305                 310                 315                 320

Glu Trp Glu Lys Arg Phe Gly Arg Lys Arg Ala Asp Pro Ser Lys Gln
            325                 330                 335

Pro Ala Leu Cys Pro Asp Phe Leu Ile Glu Thr Tyr Leu Asp His Ala
            340                 345                 350

Gly Glu Lys Phe Cys Leu Glu Tyr Asp Pro Asn Ser Leu Leu Tyr Val
            355                 360                 365

Ser Lys Ala Met Asp Leu Phe Asp Leu Gly Gln Ala Gln Gln Thr Glu
            370                 375                 380

Thr Lys Lys Arg Arg Ala Glu Tyr Glu Ala Asn Ile Ala Glu Gly Gly
385                 390                 395                 400

Lys Thr Val Asp Ala Ser Asn Ile Ala Cys Ser Leu Thr Leu Pro Glu
                405                 410                 415

Lys Pro Tyr Glu Glu Gln Pro Ser Val Thr Ala Ser Thr Pro Ala Met
            420                 425                 430

Asp Gln Ser Val Thr Gly Gly Ala Glu Ala Pro Pro Gln Asp Leu Val
            435                 440                 445

Ala Gly Leu Ala Pro Leu Lys Asn His Pro Val Leu Val Met Gly Val
            450                 455                 460

Ala Ser Asp Ile Leu Phe Pro Ala Trp Gln Gln Leu Glu Ile Ala Glu
465                 470                 475                 480

Thr Leu Arg Ala Gly Gly Asn Glu Lys Val Gln His Ile Glu Leu Gly
                485                 490                 495

Glu Asp Val Ser Met Phe Gly His Asp Thr Phe Leu Leu Asp Leu Lys
            500                 505                 510

Asn Ile Gly Gly Ala Val Glu Lys Phe Leu Arg
            515                 520

<210> SEQ ID NO 7
<211> LENGTH: 371
<212> TYPE: PRT
<213> ORGANISM: Aspergillus sojae

<400> SEQUENCE: 7

```
Met Phe Arg Gln Ser Ile Arg Arg Phe Gly Thr Thr Ala Leu Arg Ala
1               5                   10                  15

Ala Glu Gly Ser Thr Ala Tyr Ser Val Arg Val Ser Gln Ala Gln Gly
            20                  25                  30

Tyr Val Asn Gly Leu Thr Glu Ala Ile Gly Asn Thr Pro Leu Ile Arg
        35                  40                  45

Leu Lys Arg Leu Ser Glu Glu Thr Gly Cys Asn Ile Leu Gly Lys Ala
50                  55                  60

Glu Phe Gln Asn Pro Gly Gly Ser Val Lys Asp Arg Ala Ala Leu Phe
65                  70                  75                  80

Val Val Lys Asp Ala Glu Glu Lys Gly Leu Leu Lys Pro Gly Gly Thr
                85                  90                  95

Val Val Glu Gly Thr Ala Gly Asn Thr Gly Ile Gly Leu Ala His Val
            100                 105                 110

Cys Arg Ser Lys Gly Tyr Lys Leu Val Ile Tyr Met Pro Asn Thr Gln
        115                 120                 125

Ser Gln Gly Lys Ile Asp Leu Leu Arg Leu Leu Gly Ala Glu Val Tyr
130                 135                 140

Pro Val Pro Ala Val Ala Phe Asp Asn Pro Gln Asn Tyr Asn His Gln
145                 150                 155                 160

Ala Arg Arg His Ala Glu Ser Leu Asp Asn Ala Val Trp Thr Asn Gln
                165                 170                 175

Phe Asp Asn Thr Ala Asn Arg Gln Ala His Ile Glu Met Thr Gly Pro
            180                 185                 190

Glu Ile Trp Ala Gln Thr Gly Gly Gln Val Asp Ala Phe Thr Cys Ala
        195                 200                 205

Thr Gly Thr Gly Gly Thr Leu Ala Gly Ile Thr Arg Tyr Leu Lys Thr
210                 215                 220

Ala Ser Asp Gly Arg Val Lys Cys Phe Leu Ala Asp Pro Pro Gly Ser
225                 230                 235                 240

Val Leu His Ser Tyr Ile Gln Ser Gly Gly Asn Leu Ile Glu Arg Ser
                245                 250                 255

Gly Ser Ser Ile Thr Glu Gly Ile Gly Gln Gly Arg Val Thr Asp Asn
            260                 265                 270

Leu Gln Pro Asp Ile Asp Leu Leu Asp Gly Ser Leu Asn Ile Ser Asp
        275                 280                 285

Glu Lys Ser Ile Glu Met Val Tyr Arg Cys Leu Asp Glu Glu Gly Leu
290                 295                 300

Tyr Leu Gly Ala Ser Ser Ala Leu Asn Val Val Ala Ala Lys Glu Val
305                 310                 315                 320

Ala Glu Lys Leu Gly Lys Gly Lys Thr Val Val Thr Ile Leu Cys Asp
                325                 330                 335

Gly Ala Tyr Arg Tyr Ala Asp Arg Leu Phe Ser Asn Thr Trp Leu Gln
            340                 345                 350

Ser Lys Gly Leu Arg Thr Ala Ile Pro Lys His Leu Glu Lys Tyr Ile
        355                 360                 365

Val Leu Pro
    370
```

<210> SEQ ID NO 8
<211> LENGTH: 276
<212> TYPE: PRT
<213> ORGANISM: Aspergillus sojae

<400> SEQUENCE: 8

Met Ser Asp Glu His Ile Ala Arg Gln Thr Ala Ser Ser Leu Asp Arg
1               5                   10                  15

Leu Glu Asn Phe Asn Phe Leu Leu Ser Arg His Asp Pro Ala Leu Ala
            20                  25                  30

Lys Ser Arg His Tyr Ser Phe Asp Ala Asp Ala Gly Leu Ala Pro
        35                  40                  45

Phe Gln Asn Leu Ser Met Asp Tyr Asp Gln Thr Glu Gly Met Gly Gly
    50                  55                  60

Ile Ser Val Ser Ser Tyr Asp Ser Ile Glu Asp Glu Arg Asn Pro Ile
65                  70                  75                  80

Asp Val Arg Gly Tyr Pro Tyr His Ala Ala Asp Lys His Ile Asn Tyr
                85                  90                  95

Ser Leu Pro Asp Gln Met Ile Ser Tyr Pro Ala His Pro Ile Tyr Pro
            100                 105                 110

Pro Ile Ser Tyr Gly Pro Asp Asp Leu Gly His Ala Pro Gly Ala Leu
        115                 120                 125

Thr Pro Ser Asp Val Ser Ser Ile Ser Pro Pro Asn Gly Gln Leu
130                 135                 140

Gly His Thr Lys Tyr Ser Thr Gln Ile Pro Gly Asp His Leu Ala Ser
145                 150                 155                 160

Ala Leu Ser Gln Glu Glu His Val Arg Ala Ala Glu Glu Asp Arg
            165                 170                 175

Arg Arg Arg Asn Thr Ala Ala Ser Ala Arg Phe Arg Met Lys Lys Lys
        180                 185                 190

Gln Arg Glu Gln Thr Leu Glu Arg Thr Val Arg Glu Thr Thr Glu Lys
    195                 200                 205

Asn Ala Thr Leu Glu Ala Arg Val Ala Gln Leu Glu Met Glu Asn Arg
210                 215                 220

Trp Leu Lys Asn Leu Leu Thr Glu Lys His Glu Ser Thr Ser Ser Arg
225                 230                 235                 240

Met Pro Pro Pro Glu Asp Ser Thr Ala Leu Asn Gln Lys Gly Asn
            245                 250                 255

Ser Gly Gly Ser Gly Gln Lys His Ile Gln Pro Lys Lys Lys Gly Val
        260                 265                 270

Gly Thr Asp Asn
        275

<210> SEQ ID NO 9
<211> LENGTH: 748
<212> TYPE: DNA
<213> ORGANISM: Aspergillus sojae

<400> SEQUENCE: 9
tgtggaccag acaggcgcca ctcggccggg ccacaactgc ttgggttttg accgggagcg    60
gaccaattaa ggactcgaac gaccgcgggg ttcaaatgca aacaagtaca acacgcagca   120
aacgaagcag cccaccactg cgttgatgcc cagtttgtct gtccgaaatc caccggaaag   180
gtggaaacat actatgtaac aatcagaggg aagaaaaatt ttttatcgac gaggcaggat   240
agtgactgat ggtggggtca tggtcgggtc tccgagcgaa agagaaccaa ggaaacaaga   300
tcaacgaggt tggtgtaccc aaaaggccgc agcaacaaga gtcatcgccc aaaagtcaac   360
agtctggaag agactccgcc gtgcagattc tgcgtcggtc ccgcacatgc gtggtggggg   420

| | |
|---|---|
| cattaccect ccatgtccaa tgataagggc ggcggtcgag ggcttaagcc cgcccactaa | 480 |
| ttcgccttct cgcttgcccc tccatataag gattcccctc cttcccctcc cacaactttt | 540 |
| ttcctctttc tctcttcgtc cgcatcagta cgtatatctt tcccccctac ctctttctca | 600 |
| ctcttcctcg attcattcca ctcttctcct tactgcacatc tgttttgctc agtacctcta | 660 |
| cgcgatcagc cgtagtatct gagcaagctt ttttacagaa tctttctagt atcttacaaa | 720 |
| gaactacaaa gttcgcacca ccttcaaa | 748 |

<210> SEQ ID NO 10
<211> LENGTH: 800
<212> TYPE: DNA
<213> ORGANISM: Aspergillus sojae

<400> SEQUENCE: 10

| | |
|---|---|
| gtaccaggag tacattggag agttctacca ttgttgctgg aatacaatga tgattagaaa | 60 |
| ccgaagagtg ttatgattcg gacggatata cgcatggcac gcatacagcg tgatacatag | 120 |
| gctgtttgct caagaattag gatttatct gaatccatgt acagagttta cttatgttag | 180 |
| tagtcaatga aatcttggct ttctaatttt gtccgatcta caaggggtag tcgatcacag | 240 |
| aacgaactag atgtgcaggg aacgatgatc acccgctctt agcaagacct ctagtagttt | 300 |
| tcgaccatag cttaacgcg aatcatgacc ctactatttt ctagattgca gaccaagtca | 360 |
| catgacaatg tcctctttga agtaggatca gtagctgatt agattcccggg aaatgaatta | 420 |
| gggctggcgt tccaactact gggagtgcc gatgttgctg tatgaaagat agtaagatta | 480 |
| ctagtgcaca gctgtagtaa ttatttactc tagattatat attccaaata ataagtaatc | 540 |
| taagatagta gacagtccta tgatatagct ccgggttcga agtcggcaaa agatatgcaa | 600 |
| tcacctgtcg ggatgatata tgtatatctg aaataccgac atcaaccatc cagtcggatc | 660 |
| agctaaacga agtatcactt ctttcgccac tgccaatcac tacttctatt aaagttcatg | 720 |
| ttacagtata agccacaaga cttatctcca gaactaactt gtgcatagga gctctgccga | 780 |
| tagccgggtg gttggatcgg | 800 |

<210> SEQ ID NO 11
<211> LENGTH: 1838
<212> TYPE: DNA
<213> ORGANISM: Aspergillus sojae

<400> SEQUENCE: 11

| | |
|---|---|
| ttgggcttat tgctatgtcc ctgaaaggat atcaaaagca ggcaaaaagc caggcataac | 60 |
| cccgcgcgga tggtacccta aggataagcc ctaatcttat ctacatgtga ctgcgtcgat | 120 |
| gtgtttggtc caaatgaggc atgtggctca ccccacaggc ggagaaacgt gtggctagtg | 180 |
| catgacggtc ccctccatag attcaattta atttttcgcg gcaattgtcg tgcagtttgt | 240 |
| atctaccgtt cattctacat attaagggtt agtaattgga catcctgatt actttgtcta | 300 |
| attactgaaa actcgaagta ctaacctact aaataagtca gtttcaacca ctaagtactc | 360 |
| atttatacaa tagttgcaga accccgcgct accctccat tgccaacatg tcttccaagt | 420 |
| cgcaattgac ctacagcgca cgcgctagca agcaccccaa tgcgctcgtg aagaagctct | 480 |
| tcgaggttgc cgaggccaag aaaaccaatg tcaccgtttc cgccgacgtg acaaccacca | 540 |
| aagagctgct ggatttggct gaccgtatgc gcaccgggga tgccacttac atatgatcta | 600 |
| gtaatggtta atggtggaat atataacagg actcggtccg tacattgccg tgatcaaaac | 660 |
| tcacatcgat atcctctccg atttcagcga agagaccatc atcggtctga aggccttgc | 720 |

```
agagaagcac aatttcctca tcttcgaaga tcgcaagttc atcgatatcg gaaacacagt    780
ccaaaagcag taccatggcg gcactctgcg catctctgag tgggcccaca tcatcaactg    840
cagtattctg cccggtgagg gtatcgtcga ggctctggcc cagactgctt cggccgagga    900
cttcccctat ggctctgaga ggggccttt gatccttgcg gagatgacat ccaagggatc     960
tttggctacc ggtcaatata ctacttcttc tgttgactat gcccggaagt ataagaagtt   1020
tgtgatggga ttcgtctcga cgcgtcacct gggcgaggtt cagtctgaag ttagctcgcc   1080
ttcggaggag gaggatttcg tcgtcttcac gacaggtgtc aacctctcct cgaagggaga   1140
caaactggga cagcaatacc agactcctga gtctgctgtt ggacgcggtg ccgactttat   1200
cattgctggt cgtggaattt atgctgctcc tgatcccgtg gaggcagcga agcggtacca   1260
gaaagaggga tgggatgcat accagaagcg tgttggtgcg caataagtag tggtgaatac   1320
gtgctctttt tatggcagta tatcgcaagt atgatgcgat tcataaattc agcagtcgaa   1380
ttctacgaga gaacgatgct aagagatacc ctctctatat gaataatatg cctgcctcga   1440
gatatggaca tattcaagat cagagttaag ggtcatgttt caaaatcaca ccaatctcca   1500
acatagacga gaattttac cggattgtct gaaggtgcag ctggagattg gtctattttc    1560
taagagtggg gtatcactaa tgtacagtcg gtcactatcg tacaaacaat cacaattata   1620
tacaagattt cccatcaccc cttactctaa catggcactt ttatccatcg agtccgagcc   1680
tagccaccat ttggtgcttt cgtagagacc aaagtataac cctgatccga cagcggccat   1740
aaacgtgttg atagcacacc ctcggaatag tcctctcggg ccatctgttc gtataatctc   1800
ccgtacggta ttgatcatcc ttttcttctg aggtgcgg                           1838

<210> SEQ ID NO 12
<211> LENGTH: 38
<212> TYPE: DNA
<213> ORGANISM: Artificial sequence
<220> FEATURE:
<223> OTHER INFORMATION: Primer

<400> SEQUENCE: 12
cggtacccgg ggatctgtgg accagacagg cgccactc                              38

<210> SEQ ID NO 13
<211> LENGTH: 40
<212> TYPE: DNA
<213> ORGANISM: Artificial sequence
<220> FEATURE:
<223> OTHER INFORMATION: Primer

<400> SEQUENCE: 13
atgtactcct ggtactttga aggtggtgcg aactttgtag                            40

<210> SEQ ID NO 14
<211> LENGTH: 28
<212> TYPE: DNA
<213> ORGANISM: Artificial sequence
<220> FEATURE:
<223> OTHER INFORMATION: Primer

<400> SEQUENCE: 14
gtaccaggag tacattggag agttctac                                         28

<210> SEQ ID NO 15
<211> LENGTH: 23
<212> TYPE: DNA
```

-continued

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
ccgatccaac cacccggcta tcg                                    23

<210> SEQ ID NO 16
<211> LENGTH: 43
<212> TYPE: DNA
<213> ORGANISM: Artificial sequence
<220> FEATURE:
<223> OTHER INFORMATION: Primer

<400> SEQUENCE: 16
gggtggttgg atcggttggg cttattgcta tgtccctgaa agg              43

<210> SEQ ID NO 17
<211> LENGTH: 39
<212> TYPE: DNA
<213> ORGANISM: Artificial sequence
<220> FEATURE:
<223> OTHER INFORMATION: Primer

<400> SEQUENCE: 17
cgactctaga ggatcccgca cctcagaaga aaaggatga                   39

<210> SEQ ID NO 18
<211> LENGTH: 25
<212> TYPE: DNA
<213> ORGANISM: Artificial sequence
<220> FEATURE:
<223> OTHER INFORMATION: Primer

<400> SEQUENCE: 18
tttgaaggtg gtgcgaactt tgtag                                  25

<210> SEQ ID NO 19
<211> LENGTH: 38
<212> TYPE: DNA
<213> ORGANISM: Artificial sequence
<220> FEATURE:
<223> OTHER INFORMATION: Primer

<400> SEQUENCE: 19
cgcaccacct tcaaaatgtc acctttggct ctctctcc                    38

<210> SEQ ID NO 20
<211> LENGTH: 37
<212> TYPE: DNA
<213> ORGANISM: Artificial sequence
<220> FEATURE:
<223> OTHER INFORMATION: Primer

<400> SEQUENCE: 20
atgtactcct ggtacctaaa gatcccgcac caggcgt                     37

<210> SEQ ID NO 21
<211> LENGTH: 23
<212> TYPE: DNA
<213> ORGANISM: Artificial sequence
<220> FEATURE:
<223> OTHER INFORMATION: Primer

<400> SEQUENCE: 21
tgtggaccag acaggcgcca ctc                                    23

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
ccgcacctca gaagaaaagg atga                                              24

<210> SEQ ID NO 23
<211> LENGTH: 40
<212> TYPE: DNA
<213> ORGANISM: Artificial sequence
<220> FEATURE:
<223> OTHER INFORMATION: Primer

<400> SEQUENCE: 23
cggtacccgg ggatcggttg aagctgtcat tgtgtgccga                             40

<210> SEQ ID NO 24
<211> LENGTH: 39
<212> TYPE: DNA
<213> ORGANISM: Artificial sequence
<220> FEATURE:
<223> OTHER INFORMATION: Primer

<400> SEQUENCE: 24
cctgtctggt ccacaaatca gctcctctgc gtgttctgc                              39

<210> SEQ ID NO 25
<211> LENGTH: 39
<212> TYPE: DNA
<213> ORGANISM: Artificial sequence
<220> FEATURE:
<223> OTHER INFORMATION: Primer

<400> SEQUENCE: 25
tcttctgagg tgcggacgaa ctacaatggt gcctggctc                              39

<210> SEQ ID NO 26
<211> LENGTH: 39
<212> TYPE: DNA
<213> ORGANISM: Artificial sequence
<220> FEATURE:
<223> OTHER INFORMATION: Primer

<400> SEQUENCE: 26
cgactctaga ggatcgcttg gtagagttgc cgcatctgt                              39

<210> SEQ ID NO 27
<211> LENGTH: 28
<212> TYPE: DNA
<213> ORGANISM: Artificial sequence
<220> FEATURE:
<223> OTHER INFORMATION: Primer

<400> SEQUENCE: 27
ttgggcttat tgctatgtcc ctgaaagg                                          28

<210> SEQ ID NO 28
<211> LENGTH: 39
<212> TYPE: DNA
<213> ORGANISM: Artificial sequence
<220> FEATURE:

<223> OTHER INFORMATION: Primer

<400> SEQUENCE: 28
gggtggttgg atcggacacc taaggctcct gagaacggt          39

<210> SEQ ID NO 29
<211> LENGTH: 39
<212> TYPE: DNA
<213> ORGANISM: Artificial sequence
<220> FEATURE:
<223> OTHER INFORMATION: Primer

<400> SEQUENCE: 29
tagcaataag cccaaagata agctcggttg cgagggagt          39

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
gtggaccaga caggcgccac tc          22

<210> SEQ ID NO 31
<211> LENGTH: 27
<212> TYPE: DNA
<213> ORGANISM: Artificial sequence
<220> FEATURE:
<223> OTHER INFORMATION: Primer

<400> SEQUENCE: 31
ttattgggac gacctggggt taagggg          27

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
ccatcccaca aacacggagg aaaca          25

<210> SEQ ID NO 33
<211> LENGTH: 26
<212> TYPE: DNA
<213> ORGANISM: Artificial sequence
<220> FEATURE:
<223> OTHER INFORMATION: Primer

<400> SEQUENCE: 33
atctgttctg gtcggaggtg tctgag          26

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
aagacgtggc aaaccactcg ca          22

```
<210> SEQ ID NO 35
<211> LENGTH: 24
<212> TYPE: DNA
<213> ORGANISM: Artificial sequence
<220> FEATURE:
<223> OTHER INFORMATION: Primer

<400> SEQUENCE: 35
ttggcttgtt ggaccgttgg ttgc                                          24

<210> SEQ ID NO 36
<211> LENGTH: 24
<212> TYPE: DNA
<213> ORGANISM: Artificial sequence
<220> FEATURE:
<223> OTHER INFORMATION: Primer

<400> SEQUENCE: 36
tacccaaaca ccacattccc gctc                                          24

<210> SEQ ID NO 37
<211> LENGTH: 24
<212> TYPE: DNA
<213> ORGANISM: Artificial sequence
<220> FEATURE:
<223> OTHER INFORMATION: Primer

<400> SEQUENCE: 37
agcttccgaa acaatggcga cgtg                                          24

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
actggtacgg ataacccatg cagca                                         25

<210> SEQ ID NO 39
<211> LENGTH: 26
<212> TYPE: DNA
<213> ORGANISM: Artificial sequence
<220> FEATURE:
<223> OTHER INFORMATION: Primer

<400> SEQUENCE: 39
atcactactc gtcgcaggtg caacac                                        26

<210> SEQ ID NO 40
<211> LENGTH: 26
<212> TYPE: DNA
<213> ORGANISM: Artificial sequence
<220> FEATURE:
<223> OTHER INFORMATION: Primer

<400> SEQUENCE: 40
aagatgatcg acctcccaag gtccca                                        26

<210> SEQ ID NO 41
<211> LENGTH: 24
<212> TYPE: DNA
<213> ORGANISM: Artificial sequence
<220> FEATURE:
<223> OTHER INFORMATION: Primer
```

```
<400> SEQUENCE: 41
agtacagttg gagtccctca cagg                                        24

<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42
ccggtcaaaa cccaagcagt tgtg                                        24

<210> SEQ ID NO 43
<211> LENGTH: 26
<212> TYPE: DNA
<213> ORGANISM: Artificial sequence
<220> FEATURE:
<223> OTHER INFORMATION: Primer

<400> SEQUENCE: 43
ccaagtcgca attgacctac agcgca                                      26

<210> SEQ ID NO 44
<211> LENGTH: 26
<212> TYPE: DNA
<213> ORGANISM: Artificial sequence
<220> FEATURE:
<223> OTHER INFORMATION: Primer

<400> SEQUENCE: 44
atcccatccc tctttctggt accgct                                      26

<210> SEQ ID NO 45
<211> LENGTH: 38
<212> TYPE: DNA
<213> ORGANISM: Artificial sequence
<220> FEATURE:
<223> OTHER INFORMATION: Primer

<400> SEQUENCE: 45
cgcaccacct tcaaaatggg atctatatac ggcgtggc                         38

<210> SEQ ID NO 46
<211> LENGTH: 42
<212> TYPE: DNA
<213> ORGANISM: Artificial sequence
<220> FEATURE:
<223> OTHER INFORMATION: Primer

<400> SEQUENCE: 46
atgtactcct ggtactcagc gcaagaattt ctctactgca cc                    42

<210> SEQ ID NO 47
<211> LENGTH: 26
<212> TYPE: DNA
<213> ORGANISM: Artificial sequence
<220> FEATURE:
<223> OTHER INFORMATION: Primer

<400> SEQUENCE: 47
gtcaatacgg gataataccg cgccac                                      26

<210> SEQ ID NO 48
<211> LENGTH: 24
```

```
<212> TYPE: DNA
<213> ORGANISM: Artificial sequence
<220> FEATURE:
<223> OTHER INFORMATION: Primer

<400> SEQUENCE: 48
acacctaagg ctcctgagaa cggt                                              24

<210> SEQ ID NO 49
<211> LENGTH: 26
<212> TYPE: DNA
<213> ORGANISM: Artificial sequence
<220> FEATURE:
<223> OTHER INFORMATION: Primer

<400> SEQUENCE: 49
ttatcccgta ttgacgccgg gcaaga                                            26

<210> SEQ ID NO 50
<211> LENGTH: 48
<212> TYPE: DNA
<213> ORGANISM: Artificial sequence
<220> FEATURE:
<223> OTHER INFORMATION: Primer

<400> SEQUENCE: 50
cggtacccgg ggatcttcac cgtatcttaa tagagaacga tccgcaac                    48

<210> SEQ ID NO 51
<211> LENGTH: 25
<212> TYPE: DNA
<213> ORGANISM: Artificial sequence
<220> FEATURE:
<223> OTHER INFORMATION: Primer

<400> SEQUENCE: 51
tgtttggatg tgtctgctgg tgtgg                                             25

<210> SEQ ID NO 52
<211> LENGTH: 28
<212> TYPE: DNA
<213> ORGANISM: Artificial sequence
<220> FEATURE:
<223> OTHER INFORMATION: Primer

<400> SEQUENCE: 52
agggtggaga gtatatgatg gtactggt                                          28

<210> SEQ ID NO 53
<211> LENGTH: 40
<212> TYPE: DNA
<213> ORGANISM: Artificial sequence
<220> FEATURE:
<223> OTHER INFORMATION: Primer

<400> SEQUENCE: 53
cgactctaga ggatcccatg agatactatg atatactaag                             40

<210> SEQ ID NO 54
<211> LENGTH: 42
<212> TYPE: DNA
<213> ORGANISM: Artificial sequence
<220> FEATURE:
<223> OTHER INFORMATION: Primer

<400> SEQUENCE: 54
```
agacacatcc aaacaatgtt ccgacaaagt attcggcgct tc          42

<210> SEQ ID NO 55
<211> LENGTH: 44
<212> TYPE: DNA
<213> ORGANISM: Artificial sequence
<220> FEATURE:
<223> OTHER INFORMATION: Primer

<400> SEQUENCE: 55
tatactctcc acccttcagg ggagcacgat gtacttctcc aagt        44

<210> SEQ ID NO 56
<211> LENGTH: 46
<212> TYPE: DNA
<213> ORGANISM: Artificial sequence
<220> FEATURE:
<223> OTHER INFORMATION: Primer

<400> SEQUENCE: 56
gggtggttgg atcggttcac cgtatcttaa tagagaacga tccgca      46

<210> SEQ ID NO 57
<211> LENGTH: 42
<212> TYPE: DNA
<213> ORGANISM: Artificial sequence
<220> FEATURE:
<223> OTHER INFORMATION: Primer

<400> SEQUENCE: 57
aggagcctta ggtgtccatg agatactatg atatactaag at          42

<210> SEQ ID NO 58
<211> LENGTH: 41
<212> TYPE: DNA
<213> ORGANISM: Artificial sequence
<220> FEATURE:
<223> OTHER INFORMATION: Primer

<400> SEQUENCE: 58
cgcaccacct tcaaaatgtc agatgagcac atcgctcgtc a           41

<210> SEQ ID NO 59
<211> LENGTH: 40
<212> TYPE: DNA
<213> ORGANISM: Artificial sequence
<220> FEATURE:
<223> OTHER INFORMATION: Primer

<400> SEQUENCE: 59
atgtactcct ggtacctagt tatcggtgcc cacacccttc             40

METHOD FOR PRODUCING SELENONEINE

CROSS-REFERENCE TO RELATED APPLICATION

This is the US National Stage of International Patent Application No. PCT/JP2019/023590, filed Jun. 14, 2019, which claims the benefit of priority to Japanese Patent Application No. 2018-114919, filed Jun. 15, 2018, the disclosure of which is incorporated herein by reference in its entirety.

BRIEF DESCRIPTION OF THE DESCRIBED SEQUENCES

The nucleic and/or amino acid sequences provided herewith are shown using standard letter abbreviations for nucleotide bases, and one letter code for amino acids, as defined in with 37 CFR 1.831 through 37 CFR 1.835. Only one strand of each nucleic acid sequence is shown, but the complementary strand is understood as included by any reference to the displayed strand. The Sequence Listing is submitted as an .txt file named 96217_303_4_seq.txt, approximately 40,000 bytes, created Dec. 22, 2020, the contents of which are incorporated by reference herein in their entirety.

TECHNICAL FIELD

The present invention relates to a method for producing selenoneine. In particular, the present invention relates to a method for producing selenoneine using a microorganism having the ability to produce selenoneine.

BACKGROUND ART

Selenoneine is an organic selenium compound that is known to have antioxidant activity and the ability to promote cell growth. The application of selenoneine to the prevention and treatment of diseases associated with selenium(Se) deficiency is expected.

Known methods for producing selenoneine include extraction of selenoneine from organs or blood of animals (See, Patent Document 1), and use of fission yeast *Schizosaccharomyces pombe* transformed with genes involved in ergothioneine biosynthesis (See, Non-Patent Document 1).

A method for producing selenoneine is known, which includes a step of applying histidine and a selenium compound to a transformant overexpressing the inserted EgtA gene (See, Patent Document 2).

CITATION LIST

Patent Document

Patent Document 1: JP5669056
Patent Document 2: WO2017/026173

Non-Patent Document

Non-Patent Document 1: PLoS One 2014 May 14; 9(5): e97774

SUMMARY OF INVENTION

Technical Problem

The methods described in Patent Document 1 and Non-Patent Document 1 cannot produce selenoneine at higher yields. These methods are unsuitable for industrial-scale production of selenoneine.

In contrast, the method described in Patent Document 2 is enable to produce selenoneine at higher yields as compared to the methods described in Patent Document 1 and Non-Patent Document 1. The method described in Patent Document 2 allows for industrial-scale production of selenoneine.

The organic selenium compounds such as selenocystine, which is used in the method described in Patent Document 2, are expensive. Therefore, the method of using the conversion of the organic selenium compounds to selenoneine is uneconomical. An inorganic selenium compound may be converted to selenoneine instead of the organic selenium compound. However, if even selenious acid is used as an inorganic selenium compound in the method described in Patent Document 2, a sufficient amount of selenoneine is not produced.

Accordingly, it is an objective of the present invention to provide a method for producing selenoneine that allows production of selenoneine at higher yields, even if an inorganic selenium compound is used as a selenium compound.

Solution to Problem

To find solutions to the above-described problems, the present inventors attempted to produce selenoneine in large quantities by adding selenious acid as a substrate to a culture medium in which fungal cells ware grown in order to efficiently produce selenoneine using selenious acid. Specifically, the method described in Patent Document 2 was modified as follows: using a (AsEgtA+AsEgtC) transformant obtained using *Aspergillus sojae* as a host organism; culturing the transformant in a medium suitable for *Aspergillus sojae* for 2 days; adding selenious acid into the culture medium; and then further culturing. However, the production of selenoneine hardly increased.

It was believed that this is because *Aspergillus sojae* is sensitive to selenious acid. Therefore, as long as selenious acid is used, it is difficult to produce selenoneine in large quantities.

Accordingly, the present inventors have repeated trial and error concerning the use of another inorganic selenium compound as a starting material in place of selenious acid. As a result, the present inventors have finally focused on a biosynthetic pathway of sulfur assimilation. Specifically, if the first biosynthetic pathway for converting sulfuric acid to hydrogen sulfide and the second biosynthetic pathway for converting hydrogen sulfide to cysteine are used, it was believed that selenoneine would be possible to be produced by using selenic acid and its salts instead of sulfuric acid.

The present inventors decided to use MetR in the first biosynthetic pathway, and SatA and CysB in the second biosynthetic pathway. MetR promotes the reaction of converting sulfuric acid to sulfurous acid and further converting sulfurous acid to hydrogen sulfide. SatA catalyzes the reaction that converts serine to acetylserine. CysB catalyzes the reaction that converts acetylserine and hydrogen sulfide to cysteine. The present inventors have prepared a transformant that overexpresses a MetR gene, a SatA gene and/or a CysB gene in addition to an EgtA gene. The present inventors have subjected selenic acid to the transformant to successfully produce selenoneine.

Surprisingly, the addition of selenic acid to the culture medium, which increased the amount of fungal cells of the transformant, allowed for a mass production of selenoneine. More surprisingly, the using of the transformant overexpressing the EgtA gene, the MetR gene, the SatA gene and the CysB gene allowed for a high selenoneine content in the resulting selenoneine extracts.

Accordingly, the present inventors have finally succeeded in creating a method for producing selenoneine in large quantities from selenic acid by using the transformant that overexpresses the gene encoding the enzyme that catalyzes the reaction that converts selenic acid to selenoneine, in addition to the EgtA gene. It is these successful examples and findings that ultimately led to the completion of the present invention.

According to one embodiment of the present invention, methods and transformants of [1] to [10] below are provided.

[1] A method for producing selenoneine, including the step of applying histidine and a selenium compound to a transformant to obtain selenoneine, wherein the transformant has at least one gene selected from the group consisting of a SatA gene, a CysB gene and a MetR gene, and an EgtA gene inserted therein and can overexpress the inserted genes.

[2] The method according to [1], wherein the transformant has two copies to eight copies of the EgtA gene inserted therein and can overexpress the inserted gene.

[3] A method for producing selenoneine, including the step of applying histidine and a selenium compound to a transformant to obtain selenoneine, wherein the transformant has two copies to eight copies of an EgtA gene inserted therein and can overexpress the inserted gene.

[4] The method according to any one, of [1] to [3], wherein the selenium compound includes at least one selenium compound selected from the group consisting of selenic acid, selenious acid, selenium chloride, selenium tetrachloride, selenium, selenium dioxide, selenides, selenium sulfide, dimethylselenium, selenophosphate and salts thereof.

[5] The method according to any one of [1] to [4] wherein a host organism of the transformant is a microorganism expressing at least one enzyme selected from the group consisting of selenic acid reductase, selenocysteine lyase and serine dehydratase.

[6] The method according of any one of [1] to [4] wherein a host organism of the transformant is at least one microorganism selected from the group consisting of microorganisms of genus *Aspergillus*, genus *Escherichia*, genus *Trichoderma*, genus *Fusarium*, genus *Penicillium*, genus *Rhizopus* and genus *Neurospora*.

[7] The method according to any one of [1] to [4], wherein a host organism of the transformant is a microorganism of the genus *Aspergillus* selected from the group consisting of *Aspergillus sojae, Aspergillus oryzae, Aspergillus niger, Aspergillus tamarii, Aspergillus luchuensis, Aspergillus usamii, Aspergillus aculeatus* and *Aspergillus saitoi*.

[8] A transformant that has at least one gene selected from the group consisting of a SatA gene, a CysB gene and a MetR gene, and an EgtA gene inserted therein and can overexpress the inserted genes.

[9] The transformant according to [8], wherein the transformant has two copies to eight copies of the EgtA gene inserted therein and can overexpress the inserted gene.

[10] A transformant that has two copies to eight copies of an EgtA gene inserted therein and can overexpress the inserted gene.

Advantageous Effects of Invention

According to the method or the transformant, which serve as one embodiment of the present invention, selenoneine can be produced at high yields from selenic acid which is an inorganic selenium compound. Therefore, the method or the transformant serving as one embodiment of the present invention allows industrial-scale production of selenoneine.

Furthermore, according to the method or the transformant, which serve as one embodiment of the present invention, selenoneine extracts with a high ratio of selenoneine relative to ergothioneine can be produced. Therefore, the method or the transformant serving as one embodiment of the present invention allows production of high selenoneine content products by simplifying a separation and/or a purification of selenoneine.

BRIEF DESCRIPTION OF DRAWINGS

FIG. 1A shows the results of measuring the amount of selenoneine in the supernatant fraction obtained from the culture medium of *Aspergillus sojae* transformant prepared in Examples 2 to 5 as described below.

FIG. 1B shows the results of measuring the amount of selenoneine in the fungal cell fraction obtained from the culture medium of *Aspergillus sojae* transformant prepared in Examples 2 to 5 as described below.

FIG. 2 shows the results of measuring the total amount of selenoneine and ergothioneine produced by the *Aspergillus sojae* transformant prepared in Examples 2 to 5 as described below.

FIG. 3 shows the results of calculating the ratio of the amount of selenoneine relative to the total amount of selenoneine and ergothioneine produced by the *Aspergillus sojae* transformant prepared in Examples 2 to 5 as described below.

FIG. 4 shows the results of evaluation of sensitivity of the *Aspergillus sojae* NBRC4239 strain against sodium selenite in Example 7 as described below.

DESCRIPTION OF EMBODIMENTS

A method and a transformant, which provides one embodiment of the present invention, will now be described in details. The technical scope of the present invention is not limited to what is described in this section; rather, the present invention may take various other forms to the extent that its objectives are achieved.

Unless otherwise specified, each term in the specification is used in the sense normally used by those skilled in the art and should not be construed as having an unduly restrictive meaning.

General Description of the Method

The method in one embodiment of the present invention includes the step of applying histidine and a selenium compound to the first transformant to obtain selenoneine, and the first transformant has at least one gene selected from the group consisting of a SatA gene, a CysB gene and a MetR gene, and an EgtA gene inserted therein and can overexpress the inserted genes. The first transformant is transformed to overexpress at least one gene selected from the group consisting of the SatA gene, the CysB gene and the MetR gene; that is, any one or two or all three of these genes, in addition to the EgtA gene.

The method in another embodiment of the present invention includes the step of applying histidine and a selenium compound to the second transformant to obtain selenoneine, and the second transformant has two copies to eight copies of an EgtA gene inserted therein and can overexpress the inserted gene. The second transformant is transformed by inserting two copies, three copies, four copies, five copies, six copies, seven copies or eight copies of the EgtA gene.

For example, a transformant with two copies of the EgtA gene inserted refers to a transformant transformed by inserting two DNA constructs prepared in such a manner that the EgtA gene is appropriately expressed in a host organism into a chromosome. As used herein, a DNA construct prepared so that a specific gene is normally expressed in a host organism is also referred to as an "expression cassette" of the gene. In principle, a transformant with two copies of the EgtA gene inserted expresses the EgtA gene independently from each of two EgtA expression cassettes.

The method in another embodiment of the present invention includes the step of applying histidine and a selenium compound to the third transformant to obtain selenoneine, and the third transformant has at least one gene selected from the group consisting of a SatA gene, a CysB gene and a MetR gene, and two copies to eight copies of EgtA gene inserted therein and can overexpress the inserted genes. The third transformant is transformed by inserting all of the genes that are overexpressed by the first transformant and the second transformant.

As used herein, when simply referring to a transformant, "transformant" refers to all of the first transformant, the second transformant and the third transformant. These transformants are another embodiment of the present invention.

As used herein, the selenium compound includes, in addition to selenium compounds themselves, salts, complexes, crosslinked products and derivatives of selenium compounds.

Without wishing to be bound by any theory or presumption, one proposed mechanism of the biosynthesis of selenoneine in fungi can be schematically represented by the Scheme [I] below. The Scheme [I] shows a reaction that produces selenoneine from histidine and selenocysteine via hercynine.

Scheme [I]

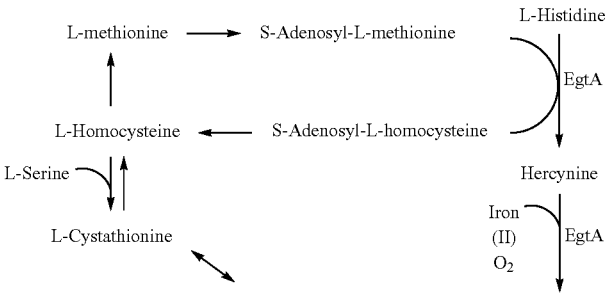

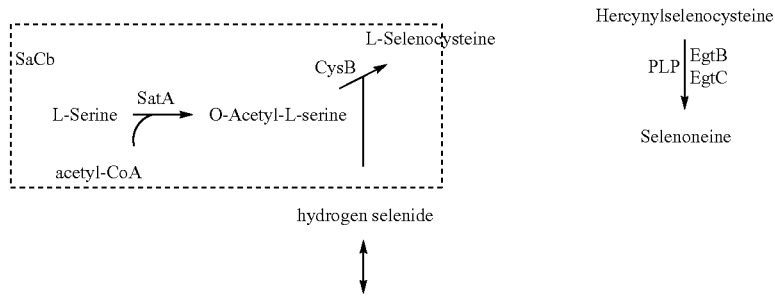

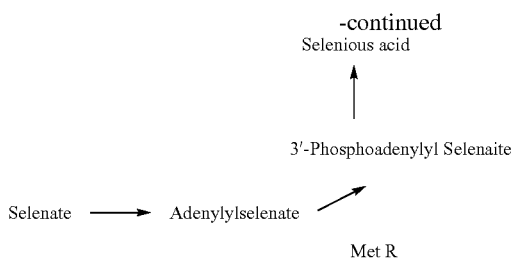

-continued wherein PLP represents pyridoxal 5'-phosphate.

EgtA, SatA, CysB and MetR in the Scheme [I] represent proteins encoded by the EgtA gene, the SatA gene, the CysB gene and the MetR gene, respectively.

As shown in the Scheme [I], the EgtA protein catalyzes the reaction in which histidine is converted to hercynine, and the reaction in which hercynine and selenocysteine are converted to hercynylselenocysteine. The SatA protein catalyzes the reaction in which serine is converted to acetylserine. The CysB protein catalyzes the reaction in which acetylserine and hydrogen selenide are converted to selenocysteine. The MetR protein works as a transcription factor, and promotes the reaction in which selenic acid is converted to selenious acid, and further the reaction in which selenious acid is converted to hydrogen selenide. The EgtB and EgtC proteins, which are encoded by the EgtB and EgtC genes, respectively, independently catalyze the reaction in which hercynylselenocysteine is converted to selenoneine.

The transformant for use of the method in another embodiment of the present invention can overexpress the EgtA, SatA, CysB and MetR genes inserted as foreign genes to ultimately produce selenoneine from histidine and a selenium compound.

Copy numbers of the SatA, CysB and MetR genes in the first and third transformants are 1 or 2 or more, respectively. The upper limit on the copy numbers is not particularly limited, but is typically about six.

In addition to the EgtA, SatA, CysB and MetR genes, other foreign genes may be inserted into the transformant. Other foreign genes are not specifically limited as long as they do not prevent the present invention from solving the present problems. Examples include EgtB and EgtC genes. The transformant may be able to efficiently produce selenoneine from hercynylselenocysteine by overexpressing the EgtB, EgtC or both genes inserted as foreign genes. In addition, the insertion of the EgtB or EgtC gene does not significantly change the productivity of selenoneine if the host organism expresses the EgtB or EgtC gene at sufficient levels.

As used herein, genes such as the EgtA, SatA, CysB and MetR genes, which are inserted and overexpressed in transformant may be referred to as inserted genes. Proteins encoded by inserted genes may be collectively referred to as inserted gene proteins.

(Inserted Gene)

An EgtA gene is not limited to any gene corresponding to the "gene encoding enzyme (1)" described in WO2017/026173 (application number: PCT/JP2016/068128). The EgtA gene can be a gene encoding the EgtA protein; that is an enzyme that has an activity to catalyze the reaction in which hercynylselenocysteine is produced from histidine and selenocysteine in the presence of S-adenosylmethionine and iron (II).

A SatA gene is not limited to any gene encoding a generally known serine O-acetyltransferase (EC2.3.1.30). Serine O-acetyltransferase has an activity to catalyze the reaction in which O-acetyl-L-serine and CoA (coenzyme A) are produced from acetyl-CoA and L-serine.

A CysB gene is not limited to any gene encoding a generally known cysteine synthase (EC2.5.1.47). Cysteine synthase has an activity to catalyze the reaction in which L-cysteine and acetic acid are produced from O-acetyl-L-serine and hydrogen sulfide. Cysteine synthase catalyzes the reaction of O-acetyl-L-serine with sulfide (s). In the present invention, this is applied to the CysB gene to obtain L-selenocysteine from O-acetyl-L-serine and hydrogen selenide (Se), which serves as selenide (Se).

Many microorganisms have been reported to have the SatA and CysB genes. For example, in the document (Microbiology (2000), 146, 2695-2703; GenBank: AAB84208.1; Curr Genet. 1997 Apr. 31(4):348-356), SatA and CysB genes in *Aspergillus nidulans* have been reported. In addition, the document (Research in Microbiology 24 Mar. 2007, 158(5):428-436) reported that many filamentous fungi enzymes have cysteine synthase activity. The assumed conversion of serine and selenic acid to selenocysteine, mediated by proteins encoded by SatA and CysB genes, is shown in the Scheme [II] below.

Scheme [II]

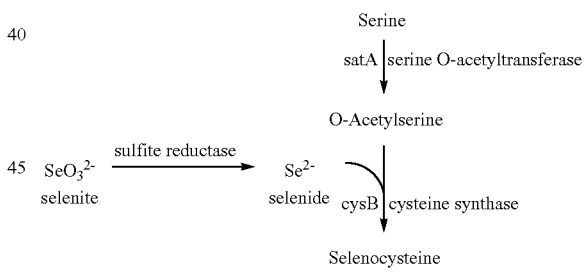

A MetR gene is not specifically limited insofar as it corresponds to "a gene comprising DNA encoding a protein having the function of regulating the expression of sulfur-assimilatory genes" as described in Patent No. JP 4029927. The MetR gene can be a gene that encodes a protein that, as a transcription factor, regulates the expression of a sulfur-assimilatory gene selected from the group consisting of arylsulfatase gene, cholinesulfatase gene, sulfate permease gene and sulfate reductase gene. The expected conversion of sulfuric acid to hydrogen sulfide by proteins encoded by the sulfur-assimilatory genes is shown in the Scheme [III] below.

Scheme [III]

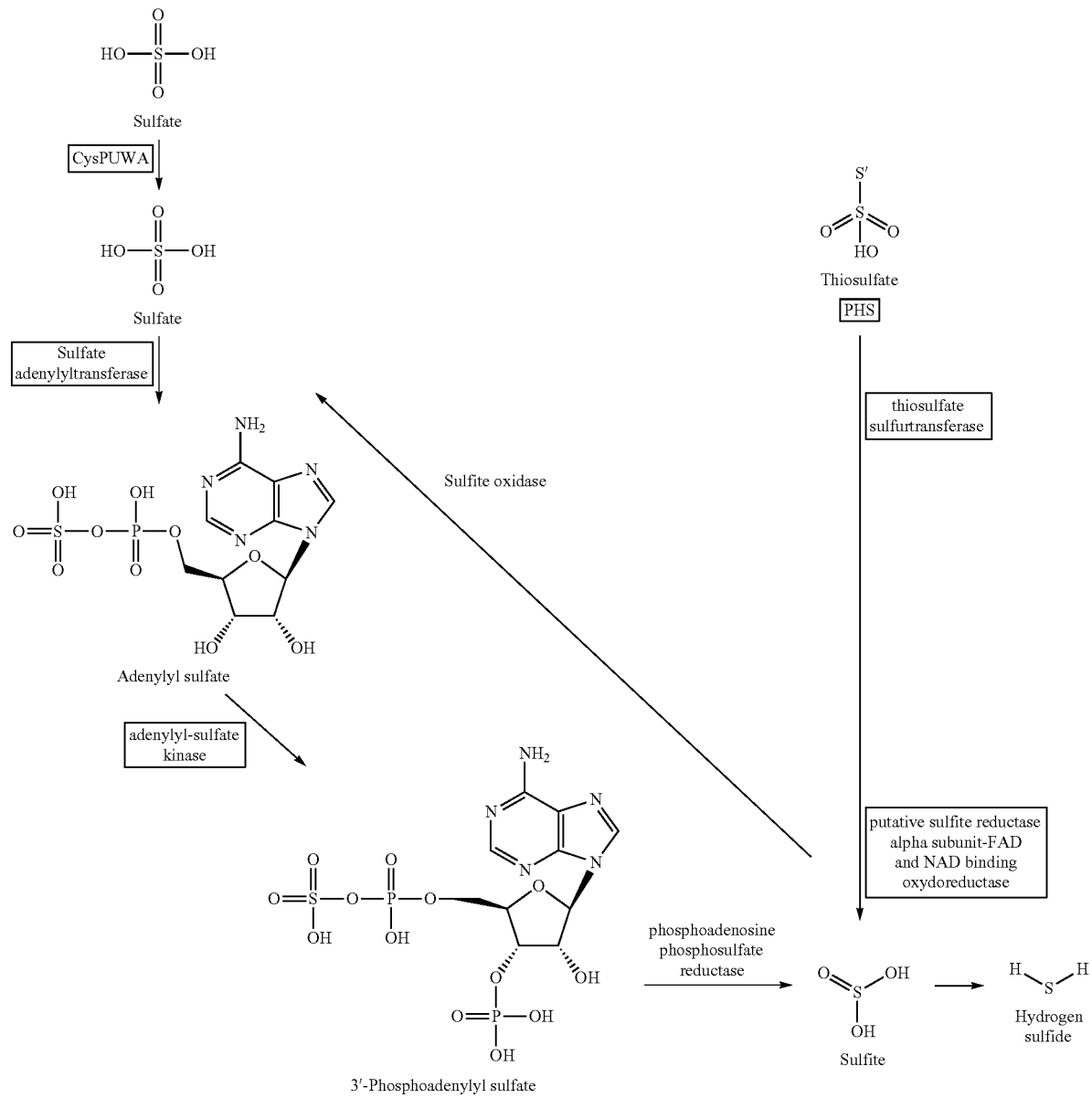

The MetR factor encoded by the MetR gene promotes the reaction in which sulfuric acid is converted to sulfurous acid, and further the reaction in which sulfurous acid is converted to hydrogen sulfide. In the present invention, this is applied to the MetR gene to obtain selenious acid from selenic acid and even hydrogen selenide. The MetR factor regulates the expression of genes encoding enzymes according to sulfur assimilation, particularly inorganic sulfur assimilation. For example, FIG. 9 in the document of Amich et al. (PLOS Pathogens, August 2013 Vol. 9, Issue 8, e1003573) provides an overview of MetR regulation in sulfur metabolism. The function of the MetR factor can prevent the oxidative conversion of selenious acid to selenic acid.

The expected biosynthetic pathway of sulfur assimilation concerning proteins encoded by the SatA, CysB and MetR genes are shown in the Scheme [IV] below. The Scheme [IV] is quoted from FIG. 9 in the above Amich et al.

Scheme [IV]

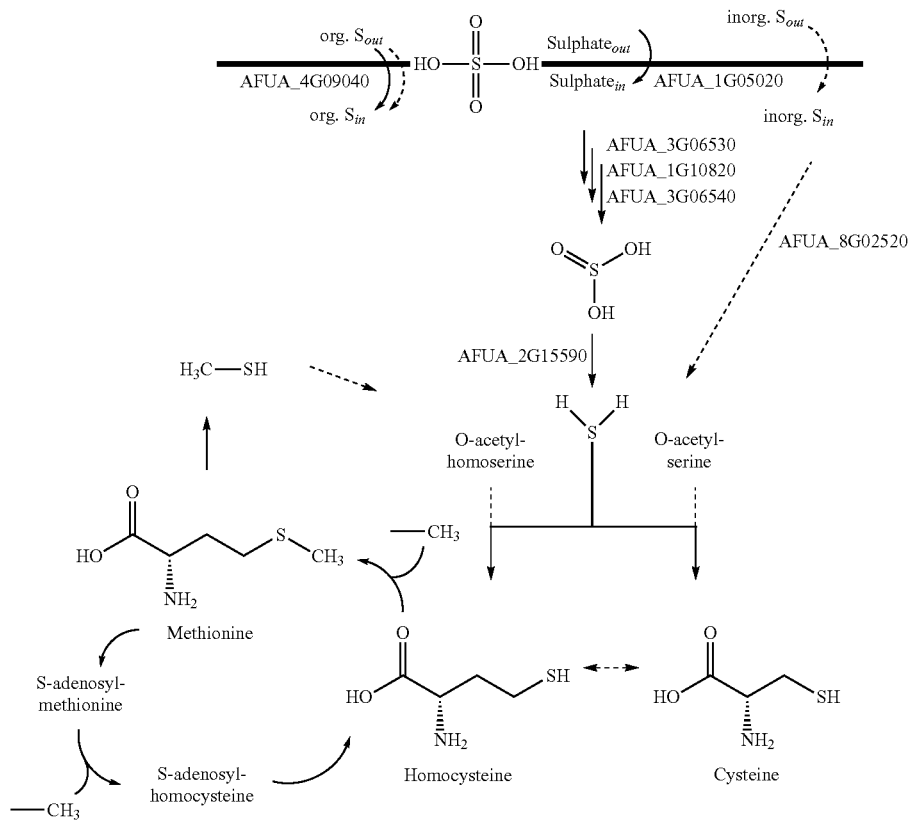

The EgtB and EgtC genes are not limited to any gene corresponding to the "gene encoding enzyme (2)" described in WO 2017/026173. The EgtB and EgtC genes can be genes encoding the EgtB and EgtC proteins; that are enzymes that has an activity to catalyze the reaction in which selenoneine is produced from hercynylselenocysteine using pyridoxal 5'-phosphate (PLP) as a coenzyme.

The inserted genes are overexpressed in the transformant to produce the inserted gene proteins. As used herein, the term "expression of a gene" means that the enzyme encoded by a gene is produced via transcription and translation in a form that exhibits its inherent activities and/or functions. As used herein, the term "overexpression of a gene" means that the protein encoded by an inserted gene is produced at a level exceeding the normal expression level of the protein in the host organism.

The inserted genes may be a gene that can produce the inserted gene proteins via splicing after the gene inserted into the host organism is transcribed, or alternatively, it may be a gene that can produce the inserted gene proteins without requiring splicing after the transcription of the gene.

The inserted genes may not be completely identical to the inherent gene (i.e., wild-type gene) of the organism of origin: it may be any DNA fragment with a nucleotide sequence that hybridizes to the nucleotide sequence complementary to the nucleotide sequence of the wild-type gene under stringent conditions as long as the gene encodes protein having at least the above-described activities and/or functions.

As used herein, "the nucleotide sequence that hybridizes under stringent conditions" refers to a sequence of DNA obtained by using a hybridization method that uses DNA fragment having the nucleotide sequence of the wild-type gene as a probe. Examples of the hybridization method include colony hybridization, plaque hybridization and southern blot hybridization.

As used herein, the term "stringent condition" refers to a condition under which the signals from specific hybrids can be clearly distinguished from the signals from non-specific hybrids. The stringent condition may vary depending on the hybridization system used, type of the probe, and the sequence and its length. Such conditions may be determined by varying the hybridization temperature or by varying the washing temperature and the salt concentration. For example, if even the signals from non-specific hybrids are strongly detected, the specificity can be increased by increasing the temperature for the hybridization and the washing temperature and if necessary, by decreasing the salt concentration for the washing. In contrast, if even the signals from specific hybrids are not detected, the hybrids may be stabilized by decreasing the temperature for the hybridization and the washing and if necessary, by increasing the salt concentration for the washing.

A specific example of the stringent condition is as follows: using a DNA probe as a probe; the hybridization is carried out overnight (approximately 8 to 16 hours) using 5×SSC, 1.0 (w/v) % blocking reagent for nucleic acid hybridization (Boehringer Mannheim), 0.1 (w/v) % N-lauroylsarcosine, and 0.02 (w/v) % SDS; the washing may be performed twice for 15 min each, using 0.1 to 0.5×SSC and 0.1 (w/v) % SDS, preferably 0.1×SSC and 0.1 (w/v) % SDS.

The temperature to carry out the hybridization and the washing is 65° C. or higher, preferably 68° C. or higher.

Examples of the DNA having a nucleotide sequence that hybridizes under stringent conditions include DNA having the nucleotide sequence of the wild-type gene originating from a colony or plaque; DNA obtained by carrying out hybridization under stringent conditions using a filter on which fragments of the DNA are immobilized; and DNA identified by carrying out hybridization at 40 to 75° C. in the presence of 0.5 to 2.0 M NaCl, preferably at 65° C. in the presence of 0.7 to 1.0 M NaCl, and subsequently washing the filter at 65° C. using 0.1 to 1×SSC solution (a 1×SSC solution contains 150 mM sodium chloride and 15 mM sodium citrate). The preparation of the probe and the hybridization can be performed according to the procedures described in textbooks such as Molecular Cloning: A laboratory Manual, 2nd-Ed., Cold Spring Harbor Laboratory, Cold Spring Harbor, NY., 1989, Current Protocols in Molecular Biology, Supplement 1-38, John Wiley & Sons, 1987-1997 (These literatures will be referred to as reference literature, hereinafter. The entire disclosure of reference literature is incorporated herein by reference). Those skilled in the art would adequately determine the conditions for obtaining DNA having a nucleotide sequence that hybridizes to the nucleotide sequence complementary to the nucleotide sequence of the wild-type gene under stringent conditions by considering, in addition to the above-mentioned conditions such as the salt concentration of buffers and the temperature, other conditions such as the probe concentrations, probe lengths, and the reaction time.

Examples of the DNA having a nucleotide sequence that hybridizes under stringent conditions include a DNA having a particular percentage or higher sequence identity to the nucleotide sequence of the DNA used as a probe having the nucleotide sequence of the wild-type gene, such as DNA having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the nucleotide sequence of the wild-type gene. The upper limit is not particularly limited, but is typically 100%.

Examples of the nucleotide sequence that hybridizes to a nucleotide sequence complimentary to the nucleotide sequence of the wild-type gene under stringent conditions include nucleotide sequences resulting from deletion, substitution, addition or other modification of from 1 to several, preferably from 1 to 50, more preferably from 1 to 30, even more preferably from 1 to 20, still even more preferably 1, 2, 3, 4, 5, 6, 7, 8, 9 or 10 nucleotides, in the nucleotide sequence of the wild-type gene, per unit consisting of 100 nucleotides. As used herein, the term "deletion of a nucleotide" means that a nucleotide is lost or eliminated from the sequence. The term "substitution of a nucleotide" means that a nucleotide is replaced with another nucleotide. The term "addition of a nucleotide" means that a new nucleotide is added to the sequence by inserting it into the sequence.

While the protein-coded by a nucleotide sequence that hybridizes to a nucleotide sequence complementary to the nucleotide sequence of the wild-type gene under stringent conditions should be a protein in having an amino acid sequence resulting from deletion, substitution, addition or other modification of to several amino acids in the amino acid sequence of the enzyme encoded by the nucleotide sequence of the wild-type gene, it has the same activities and/or functions as the protein encoded by the nucleotide sequence of the wild-type gene.

The amino acid sequence of the inserted gene protein may be any amino acid sequence resulting from deletion, substitution, addition or other modification of one to several amino acids in the amino acid sequence of the wild-type enzyme as long as it has the same activities and/or functions as the protein encoded by the inserted gene. As used herein, the range specified by the phrase "one to several" as in "deletion, substitution or addition of one to several amino acids" in the amino acid sequence is not particularly limited but specifically refers to, in the amino acid sequence, per unit consisting of 100 amino acids, 1, 2, 3, 4, 5, 6, 7, 8, 9, 10, 11, 12, 13, 14, 15, 16, 17, 18, 19, or 20 amino acids, preferably 1, 2, 3, 4, 5, 6, 7, 8, 9, or 10 or so amino acids, more preferably 1, 2, 3, 4, or 5 or so amino acids. As used herein, the term "deletion of amino acids" means that amino acid residues are lost or eliminated from the sequence. The term "substitution of amino acids" means that amino acid residues are replaced with other amino acid residues. The term "addition of amino acids" means that new amino acid residues are added to the sequence by inserting them into the sequence.

Specific examples of "deletion, substitution or addition of one to several amino acids" include embodiments in which one to several amino acids are replaced with other chemically similar amino acids. For example, a hydrophobic amino acid may be substituted with another hydrophobic amino acid, or a polar amino acid may be substituted with another polar amino acid having the same charge. Such chemically similar amino acids are known in the art for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine and cysteine. Examples of positively charged basic amino acids include arginine, histidine and lysine. Examples of negatively charged acidic amino acids include aspartic acid and glutamic acid.

Examples of the amino acid sequences resulting from deletion, substitution, addition or other modification of one to several amino acids in the amino acid sequence of the wild-type enzyme include amino acid sequences having a particular percentage or higher sequence identity to the amino acid sequence of the wild-type enzyme, such as amino acid sequences having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the amino acid sequence of the wild-type enzyme.

(Means for Determining Sequence Identity)

While the sequence identity between nucleotide sequences or amino acid sequences may be determined by any method, it can be determined by using a commonly known method, whereby a wild-type gene or an amino acid sequence of an enzyme encoded by the wild-type gene is aligned with a nucleotide sequence or amino acid sequence of interest and the percent match between the two sequences is calculated using a program.

The algorithm of Karlin and Altschul is a known program for determining the percent match between two amino acid sequences or nucleotide sequences (Proc. Natl. Acad. Sci. USA 87: 2264-2268, 1990; Proc. Natl. Acad. Sci. USA 90: 5873-5877, 1993). Using this algorithm, Altschul et al. developed the BLAST program (J. Mol. Biol. 215: 403-410, 1990). The Gapped BLAST program, which can determine the sequence identity in a more sensitive way than the BLAST, is also known (Nucleic Acids Res. 25: 3389-3402, 1997). Using the above-described programs, one skilled in the art can search in a database for a sequence with a high sequence identity to a given sequence. These programs are available on the website of U.S. National Center for Biotechnology Information (blast.ncbi.nlm.nih.gov/Blast.cgi).

While the above-described methods are commonly used in the search of sequences with certain sequence identities from a database, Genetyx network model, version 12.0.1 (Genetyx corporation) may also be used in a homology analysis to determine the sequence identity of individual sequences. This method is based on the Lipman-Pearson method (Science 227:1435-1441, 1985). When analyzing the sequence identity of nucleotide sequences, regions encoding proteins (CDS or ORF) are used when possible.

(Origins of Inserted Genes)

The inserted genes are, for example, derived from species having the ability to produce selenoneine or the ability to produce ergothioneine, or species expressing the inserted genes. Examples of the organisms of origin from which the inserted genes are derived include microorganisms. Of various microorganisms, filamentous fungi are preferred since many of their species are known to have the ability to produce ergothioneine. Examples of the filamentous fungi include fungi of the genus *Aspergillus*. Specific examples include *Aspergillus sojae, Aspergillus oryzae, Aspergillus niger, Aspergillus tamarii, Aspergillus luchensis, Aspergillus usamii, Aspergillus aculeatus, Aspergillus saitoi* and *Aspergillus nidulans*.

*Aspergillus sojae, Aspergillus oryzae, Aspergillus niger, Aspergillus tamarii, Aspergillus luchensis, Aspergillus usamii, Aspergillus aculeatus* and *Aspergillus saitoi* listed above as specific examples of the filamentous fungi of the genus *Aspergillus* have long been used in the production of miso paste, soy sauce, Japanese sake, shochu liquor and other fermented products, as well as in the production of citric acid and enzymes such as amylases. Their high enzyme productivity and high reliability for the safety, backed by a long history of use, make these microorganisms highly useful in industrial applications.

As described above, while the organisms of origin from which the inserted genes are derived are not particularly limited, the inserted: gene proteins expressed in the transformant might not be deactivated by the growth conditions of the host organisms or the proteins might show their respective activities or functions. For this reason, it is preferred that the organism of origin from which the inserted genes are derived be a microorganism that grows under conditions similar to the growth conditions of a host organism to be transformed by the insertion of the inserted genes.

(Cloning of Inserted Genes Using Genetic Engineering Technique)

The inserted genes can be inserted into various suitable known vectors. The resulting vector can then be introduced into a suitable known host organism to create a transformant in which the recombinant vector (recombinant DNA) containing the inserted genes has been introduced. A person skilled in the art can appropriately select a suitable method for obtaining the inserted genes, a method for obtaining the inserted gene sequence information and the amino acid sequence information of the inserted gene protein, as well as a method for creating different vectors and a method for creating transformants. The terms "transformation" and "transformant" as used herein encompass transduction and transductants, respectively. One non-limiting example of cloning of the inserted genes will be described below.

Cloning of the inserted genes may suitably use commonly used gene cloning techniques. For example, using a standard technique such as the technique described in the reference literature, the chromosomal DNA and mRNA can be extracted from microorganisms and various cells capable of producing the inserted gene proteins. The extracted mRNA can be used as a template to synthesize cDNA. The resulting chromosomal DNA and cDNA may be used to construct a library of chromosomal DNA or cDNA.

For example, inserted genes can be obtained by cloning from the chromosomal DNA or cDNA derived from microorganisms having the genes, which serves as a template. The organisms of origin from which the inserted genes are derived are as described above; specific examples include *Aspergillus sojae* NBRC4239 strain and *Aspergillus oryzae* RIB40 strain. For example, the *Aspergillus sojae* NBRC4239 strain is cultured and the resulting fungal cells are dehydrated and physically triturated using a mortar while chilled in liquid nitrogen to form fine powder-like cells debris, from which a fraction containing chromosomal DNA is extracted using a standard technique. A commercially available DNA extraction kit such as DNeasy Plant Mini Kit (Qiagen) can be used to extract the chromosomal DNA.

Subsequently, a polymerase chain reaction (referred to as PCR, hereinafter) was conducted using the chromosomal DNA as a template along with synthetic primers complementary to the sequences at the 5' and 3' ends. The primers are not particularly limited as long as they can amplify DNA fragments containing the inserted gene. Examples of the primers include primers shown in SEQ ID NOs: 19 to 20, 45 to 46, 54 to 55 and 58 to 59 designed based on the genome sequence of *Aspergillus sojae*. These primers can amplify the full length of the target gene and can therefore eliminate the need for RACE. Alternatively, DNA sequences containing fragments of the target gene may be amplified using suitable PCR techniques such as 5' RACE and 3' RACE and these sequences are subsequently ligated to obtain a DNA segment containing the full length target gene.

The method for obtaining the inserted gene is not particularly limited; for example, rather than using genetic engineering techniques, the inserted gene may be constructed by chemical synthesis.

For example, the nucleotide sequences of the amplification products amplified by PCR and the chemically synthesized genes may be determined as follows. First, the DNA segment to be sequenced is inserted into a suitable vector according to the standard technique to prepare a recombinant DNA. For cloning into a vector, a commercially available kit, such as TA Cloning Kit (Invitrogen); commercially available plasmid vector DNA, such as pUC119 (Takara Bio), pUC18 (Takara Bio), pBR322 (Takara Bio), pBluescript SK+(Stratagene), and pYES2/CT (Invitrogen); and commercially available bacteriophage vector DNA, such as λEMBL3 (Stratagene), may be used. The recombinant DNA is then used to transform host organisms, such as *Escherichia coli*, preferably *E. coli* JM109 strain (Takara Bio) and *E. coli* DH5α strain (Takara Bio). The recombinant DNA present in the transformant is then purified using a purification kit such as QIAGEN Plasmid Mini Kit (Qiagen).

The nucleotide sequences of genes inserted in the recombinant DNA are then determined by the dideoxy sequencing technique (Methods in Enzymology, 101, 20-78, 1983). The sequence analyzer used to determine the nucleotide sequence is not particularly limited; for example, Li-COR MODEL 4200L sequencer (Aloka), 370DNA sequencing system (Perkin Elmer), CEQ2000XL DNA analysis system (Beckman) may be used. The determined nucleotide sequences may then be used to estimate the amino acid sequence of the translated proteins, thus, the inserted gene proteins.

(Construction of a Recombinant Vector Containing Inserted Genes)

Recombinant vectors containing the inserted genes (recombinant DNA) can be constructed by connecting a PCR amplification product containing any of the inserted genes with any of various vectors in such a manner that the recombinant vector can express the inserted genes. For example, such a recombinant vector may be constructed by excising a DNA fragment containing any of the inserted genes with appropriate restriction enzyme and ligating the DNA fragment into a plasmid cut with appropriate restriction enzyme. The recombinant vector may also be obtained by connecting a DNA fragment containing the gene and having sequences homologous to a plasmid attached to the both ends with a DNA fragment derived from the plasmid amplified by inverse PCR using a commercially available recombinant vector preparation kit such as In-Fusion HD Cloning Kit (Clontech).

(Method for Creating a Transformant)

The method for creating a transformant is not particularly limited. For example, a transformant can be created by inserting a gene into a host organism in which the inserted genes are expressed according to standard method. Specifically, a DNA construct in which any of the inserted genes has been inserted between an expression-inducing promoter and a terminator is constructed. Subsequently, a host organism is transformed with the DNA construct containing the inserted genes to obtain a transformant that overexpresses the inserted genes. In the present specification, DNA fragments comprising an expression-inducing promoter—inserted genes—a terminator and recombinant vectors containing the DNA fragment that are prepared to transform the host organism are collectively referred to as "DNA constructs" or "inserted gene expression cassettes."

The method for inserting the inserted genes in a host organism in such a manner that the inserted genes are expressed in the host organism is not particularly limited. For example, the gene may be directly inserted into the chromosome of the host organism by making use of homologous recombination or non-homologous recombination, or the gene may be connected to a plasmid vector, which in turn is introduced into the host organism.

In the method that makes use of homologous recombination, a DNA construct may be connected between sequences homologous to the upstream region and the downstream region of a recombination site on a chromosome and inserted into the genome of the host organism. As a result of this self-cloning, a transformant can be obtained in which the gene is overexpressed under control of a high expression promoter in the DNA construct. The high expression promoter may be any high expression promoter, including, for example, a promoter region of translation elongation factor TEF1 gene (tef1), a promoter region of α-amylase gene (amy), a promoter region of alkaline protease gene (alp), and other suitable promoters.

In the method that makes use of a vector, a DNA construct is integrated into a plasmid vector used to transform host microorganisms using a standard method and a corresponding host organism can be transformed with the plasmid vector according to a standard method.

A suitable vector—host system may be any system that allows the production of the inserted gene proteins in the host organisms, including, for example, a system based on pUC19 and a filamentous fungus, and a system based on pSTA14 (Mol. Gen. Genet. 218, 99-104, 1989) and a filamentous fungus.

While the DNA construct is preferably introduced into the chromosome of the host organisms, it may be used without introducing into the chromosome by integrating into a self-replicating vector (Ozeki et al. Biosci. Biotechnol. Biochem. 59, 1133 (1995)).

The DNA construct may contain a marker gene that allows the selection of transformed cells. Examples of the marker gene include, but are not limited to, genes compensating for the nutritional requirements of the host organisms, such as pyrG, niaD and adeA; and drug-resistant genes such as those against pyrithiamine, hygromycin B and oligomycin. Also, the DNA construct preferably contains a promoter, a terminator and other regulatory sequences (such as enhancer and polyadenylated sequences) that enable the overexpression of the inserted genes in the host organisms. The promoter may be any suitable expression-inducing promoter or constitutive promoter, including, for example, tef1 promoter, alp promoter, and amy promoter. The terminator may also be any terminator, including, for example, alp terminator, amy terminator, and tef1 terminator.

The regulatory sequences for the inserted genes in the DNA construct are not necessarily required if the DNA fragments containing the inserted genes contain sequences having expression regulatory functions. Also, when transformation is performed by the cotransformation method, the DNA construct may not contain any marker genes.

Purification tags of the inserted gene proteins may be added to the DNA construct. For example, a suitable linker sequence may be added to the upstream or downstream of the inserted genes and six or more codons of histidine-encoding nucleotide sequences may be added to the linker to enable the purification on a nickel column.

One example of the DNA construct is a DNA construct in which a tef1 gene promoter, an inserted gene, an alp gene terminator and a pyrG marker gene are connected to the In-Fusion cloning Site located in the multiple cloning site of pUC19.

Any properly selected method known to those skilled in the art may be used for transformation into filamentous fungi; for example, the protoplast PEG technique in which protoplasts of a host organism are prepared and polyethylene glycol and calcium chloride are added may be used (See, for example, Mol. Gen. Genet. 218, 99-104, 1989, Japanese Unexamined Patent Application Publication No. 2007-222055). The medium to regenerate the transformant is properly selected depending on the host organism and the transformation marker gene used. For example, when *Aspergillus sojae* is used as the host organism and pyrG gene is used as the transformation marker gene, the transformant can be regenerated in a Czapek-Dox minimal medium (Difco) containing 0.5% agar and 1.2M sorbitol.

Alternatively, in order to obtain the transformant, the endogenous promoter for the inserted genes present on the chromosome of the host organism may be substituted with a high expression promoter such as tef1 by homologous recombination. Again, a transformation marker gene such as pyrG is preferably inserted in addition to the high expression promoter. For example, a transformation cassette consisting of the upstream region of the inserted genes—a transformation marker gene—a high expression promoter—all or a part of the inserted genes may be used for this purpose (see Example 1 and FIG. 1 of Japanese Unexamined Patent Application Publication No. 2011-239681). In this case, the upstream region of the inserted genes and all or a part of the inserted genes are used in homologous recombination. The all or a part of the inserted genes used may include a region of the gene extending from the start codon to somewhere down the length of the gene. A suitable length of the region is preferably 0.5 kb or longer for homologous recombination.

The creation of the transformant can be confirmed by the following procedure: the transformant may be cultured under a condition that induces the activities or functions of the inserted gene proteins and subsequently the resulting culture may be examined for the presence of selenoneine; or alternatively, a comparison may be made to determine if the amount of selenoneine present in the resulting culture is greater than the amount of selenoneine present in a culture of the host organism cultured under the same condition.

The creation of the transformant can be also confirmed by the following procedure: chromosomal DNA is extracted from the transformant and PCR is performed using the chromosomal DNA as a template to detect the presence of any PCR product that can be amplified if the transformation has occurred.

For example, a PCR can be performed using a combination of a forward primer for the nucleotide sequence of the promoter used and a reverse primer for the nucleotide sequence of the transformation marker gene and whether the product having an expected length is produced is determined.

When the transformation is carried out by homologous recombination, it is preferred to perform a PCR using a forward primer located upstream of the upstream homologous region used and a reverse primer located downstream of the downstream homologous region used and then determine whether the product having a length expected when the homologous recombination has occurred is produced.

By inserting a second inserted gene into the transformant in which the first inserted gene is inserted, a transformant in which the first inserted gene and the second inserted gene are inserted can be prepared. By repeating this procedure, a transformant with multiple inserted genes can be prepared.

When preparing a transformant in which multiple inserted genes are inserted, if the marker gene inserted together with the first inserted gene and the marker gene inserted together with the second inserted gene are the same, it is preferable to remove the marker gene inserted together with the first inserted gene after the first inserted gene is inserted.

For example, in an inserted gene expression cassette containing a first inserted gene, a region for looping out and a marker gene which are linked in order, if a region with the same sequence as the region for looping out is present in downstream of a site on the host organism's chromosome that can be introduced by homologous recombination, the inserted gene expression cassette is inserted onto the host organism's chromosome due to homologous recombination that occurs between the region for looping out and the same sequence region downstream so that the marker gene can be removed by looping out. After the first inserted gene has been inserted, a transformant can be obtained in which the inserted marker gene along with the first inserted gene is removed.

(Host Organism)

The host organism is not limited to any microorganism that can produce the inserted gene proteins when transformed by a DNA construct containing the inserted genes. An example thereof is a microorganism capable of metabolizing selenium in view of the toxicity of the selenium compound. The host organism is preferably microorganisms that can express selenic acid reductase (EC1.97.1.9), selenocysteine lyase (EC4.4.1.16), serine dehydratase (EC4.3.1.17) or two or more of those enzymes, more preferably filamentous fungi such as the genus *Aspergillus*, the genus *Escherichia*, the genus *Trichoderma*, the genus *Fusarium*, the genus *Penicillium*, the genus *Rhizopus* and the genus *Neurospora*, photosynthetic microorganism and probiotic microorganism.

For example, it is known that microorganisms such as the genus *Acinetobacter*, the genus *Aeromonas*, the genus *Arthrobacter*, the genus *Bacillus*, the genus *Candida*, the genus *Cephalosporium*, the genus *Citrobacter*, the genus *Corynebacterium*, the genus *Flavobacterium*, the genus *Fusarium*, the genus *Micrococcus*, the genus *Neurospora*, the genus *Penicillium*, the genus *Pseudomonas*, the genus *Salmonella*, the genus *Scopulariopsis*, the genus Selenomonas have an oxidation or reducing ability for selenium compound (refer to D. T. Maiers et al., APPLIED AND ENVIRONMENTAL MICROBIOLOGY, October 1988, p.2591-2593). Especially, selenate reductase or the gene encoding the enzyme is found from *Thauera selenatis*, *Escherichia coli*, *Enterobacter cloacae* and *Bacillus selenatarsenatis* (refer to SAKAGUCHI Toshifumi, "selenium oxyanion reductase and its gene", Biomedea, 2012 Vol. 3, p.133). Also, it is known that *Alcaligenes* viscolactis, *Escherichia freundii*, *Corynebacterium pseudodiphtheriticum*, *Pseudomonas alkanolytica*, *Brevibacterium leucinophagum*, *Escherichia coli*, *Erwinia carotovora*, *Serratia marcescens*, *Alcaligenes bookeri*, *Aspergillus ficuum*, *Aspergillus sojae*, *Absidia corymbifera*, *Neurospora crassa*, *Penicillium expansum*, *Saccharomyces cerevisiae*, *Kluyveromyces fragilis*, *Candida albicans*, *Hansenula beckii* and *Schwanniomyces occidentalis* have a selenocysteine lyase activity or a possibility of said activity (refer to PATRICK CHOCAT et al., JOURNAL OF BACTERIOLOGY, October 1983, p.455-457). Thus, those microorganisms can be used as host organisms. Also, beyond those microorganisms, any other microorganisms having the reinforced selenium metabolism gene or the expression of the heterologous gene can be used as host organisms. Further, it may be possible that the microorganism can be used as the organism of origin from which the inserted genes are derived.

Among them, the host organism is more preferably any of the microorganisms of filamentous fungi in which the production of ergothioneine is detected and filamentous fungi that have the inserted genes on their genomic DNA. Specific examples of the filamentous fungi include filamentous fungi described in Donald et al. document (Donald B. Melville et al., J. Biol. Chem. 1956, 223:9-17, the entire disclosure of which is incorporated herein by reference) and Dorothy et al. document (Dorothy S. Genghof, J. Bacteriology, August 1970, p.475-478, the entire disclosure of which is incorporated herein by reference), such as filamentous fungi belonging to the genus *Aspergillus*, the genus *Neurospora*, the genus *Penicillium*, the genus *Fusarium*, the genus *Trichoderma*, and the genus *Mucor*. Examples of the filamentous fungi that have inserted genes on their genomic DNA include filamentous fungi belonging to the genus *Neosartorya*, the genus *Byssochlamys*, the genus *Talaromyces*, the genus *Ajellomyces*, the genus *Paracoccidioides*, the genus *Uncinocarpus*, the genus *Coccidioides*, the genus *Arthroderma*, the genus *Trichophyton*, the genus *Exophiala*, the genus *Capronia*, the genus *Cladophialophora*, the genus *Macrophomina*, the genus *Leptosphaeria*, the genus *Bipolaris*, the genus *Dothistroma*, the genus *Pyrenophora*, the genus *Neofusicoccum*, the genus *Setosphaeria*, the genus *Baudoinia*, the genus *Gaeumannomyces*, the genus *Marssonina*, the genus *Sphaerulina*, the genus *Sclerotinia*, the genus *Magnaporthe*, the genus *Verticillium*, the genus *Pseudocercospora*, the genus *Colletotrichum*, the genus *Ophiostoma*, the genus *Metarhizium*, the genus *Sporothrix* and the genus *Sordaria*.

Of these filamentous fungi, in terms of the safety and easy culturing, the host filamentous fungus is preferably any of the microorganisms of the genus *Aspergillus* listed above as the organisms of origin from which the inserted genes are derived, including *Aspergillus sojae, Aspergillus oryzae, Aspergillus niger, Aspergillus tamarii, Aspergilius luchensis, Aspergilius usamii, Aspergillus aculeatus, Aspergilius saitoi* and *Aspergillus nidulans*.

The host organism may be a wild strain or a transformant obtained by transforming the wild strain in advance. The transformant obtained by transforming a wild strain in advance to be used as a host organism is not particularly limited.

Filamentous fungi, including the microorganisms of the genus *Aspergillus* tend to have a low frequency of homologous recombination. Therefore, in case that the transformant is prepared by homologous recombination, it is preferable to use transformed filamentous fungi in which Ku genes such as Ku70 and Ku80 involved in the non-homologous recombination mechanism is suppressed.

Such suppression of the Ku gene can be carried out by any method known to those skilled in the art. For example, the Ku gene can be suppressed by disrupting the Ku gene using a Ku gene disruption vector, or by inactivating the Ku gene by an antisense RNA method using an antisense expression vector of the Ku gene. The homologous recombination frequency of the transformed microorganisms of the genus *Aspergillus* obtained is markedly increased compared to the homologous recombination frequency of the original microorganisms of the genus *Aspergillus* prior to the genetic manipulation of the Ku gene for suppression, specifically at least 2-fold, preferably at least 5-fold, preferably at least 10-fold, preferably at least about 50-fold increased.

As a host organism, it is preferable to use a transformant in which a marker gene such as pyrG is suppressed. The marker gene to be suppressed can be appropriately selected according to the marker gene to be included in the DNA construct.

(Specific Examples of Inserted Genes)

Examples of the inserted genes derived from the *Aspergillus sojae* NBRC4239 strain include AsEgtA, AsSatA, AsCysB and AsMetR genes which will be described in Examples below. The nucleotide sequences of the AsEgtA, AsSatA, AsCysB and AsMetR genes are shown in SEQ ID NOs: 1 to 4 in the sequence listing, respectively. Further, the amino acid sequences of the AsEgtA, AsSatA, AsCysB and AsMetR proteins are shown in SEQ ID NOs: 5 to 8 in the sequence listing, respectively.

Inserted genes may be obtained from microorganisms other than those of *Aspergillus sojae* by any suitable method. For example, a homology search by BLAST may be conducted on the genomic DNA of microorganisms other than those of *Aspergillus sojae* based on the nucleotide sequences of the AsEgtA, AsSatA, AsCysB and AsMetR genes (SEQ ID NOs: 1 to 4) and the amino acid sequences of the AsEgtA, AsSatA, AsCysB and AsMetR proteins (SEQ ID NOs: 5 to 8), to identify genes having a nucleotide sequence with a high sequence identity to the nucleotide sequences of the AsEgtA, AsSatA, AsCysB and AsMetR genes. Alternatively, inserted genes may be obtained by identifying proteins having a high sequence identity to the AsEgtA, AsSatA and AsMetR proteins from the total protein of microorganisms other than those of *Aspergillus sojae* and identifying the genes encoding these proteins. Whether the resulting genes are equivalent to the inserted genes can be determined by transforming the organism of origin as the host organism with the obtained gene and determining if selenoneine is produced or determining if the production of selenoneine is enhanced compared to the host organisms.

For example, the EgtA gene derived from *Aspergillus oryzae* RIB40 strain include the AoEgtA gene of SEQ ID NO: 23 in the sequence listing in WO2017/026173. The amino acid sequence of the AoEgtA protein is listed in WO2017/026173 as SEQ ID NO: 24 in the sequence listing.

Since *Aspergillus sojae, Aspergillus oryzae* and *Aspergillus niger* grow under similar conditions, it may be possible to transform these microorganisms each other by inserting the gene possessed by one of these microorganisms into one of these microorganisms. For example, an inserted gene derived from *Aspergillus sojae* may be inserted into the host organism of *Aspergillus oryzae* or *Aspergillus niger* to transform them. In order to ensure that the inserted gene proteins have the desired enzymatic activity, it is preferred that the organism of origin from which the inserted genes are derived and the host organism are identical. For example, an inserted gene derived from *Aspergillus sojae* may be inserted into the same *Aspergillus sojae*.

The inserted genes may be genes optimized for their codons, secondary structures and GC contents based on the amino acid sequence of the inserted gene proteins derived from *Aspergillus sojae*. Specific examples of such genes include EcEgtA and EcEgtC synthesized for expression in *E. coli*, which are described as SEQ ID NOs: 27 and 28 in the sequence listing in WO2017/026173.

(One embodiment of transformant) One embodiment of the transformant is an *Aspergillus sojae* transformant obtained by inserting two copies to four copies of the AsEgtA gene into *Aspergillus sojae* for overexpression of the AsEgtA protein. Another embodiment of the transformant is an *Aspergillus sojae* transformant obtained by inserting one copy to four copies of the AsEgtA gene, one copy to two copies of the AsSatA gene and one copy to two copies of the AsCysB gene into *Aspergillus sojae* for overexpression of the AsEgtA, AsSatA and AsCysB proteins. Another embodiment of the transformant is an *Aspergillus sojae* transformant obtained by inserting one copy to four copies of the AsEgtA gene and one copy to two copies of the AsMetR gene into *Aspergillus sojae* for overexpression of the AsEgtA and AsMetR proteins. Another embodiment of the transformant is an *Aspergillus sojae* transformant obtained by inserting one copies to four copies of the AsEgtA gene, one copy to two copies of the AsSatA gene, one copy to two copies of the AsCysB gene and one copies to two copies of the AsMetR gene into *Aspergillus sojae* for overexpression of the AsEgtA, AsSatA AsCysB and AsMetR proteins. Another embodiment of the transformant is an *Aspergillus oryzae* transformant obtained by inserting two copies to four copies of the AsEgtA gene into *Aspergillus oryzae* for overexpression of the AsEgtA protein.

The above-mentioned *Aspergillus sojae* and *Aspergillus oryzae* transformants are designed to overexpress the inserted gene proteins and are capable of produce selenoneine at detectable or higher levels while the respective host organisms can produce little or no selenoneine. In addition, the *Aspergillus sojae* and *Aspergillus oryzae* transformants can produce selenoneine not only from organic selenium compounds such as selenocysteine and selenocystine, but also from inorganic selenium compounds such as selenious acid, as will be described later in Examples. Accordingly, the transformant is preferably a transformant in which the expression of the inserted genes is enhanced such that the amount of selenoneine is increased as compared to the host organism.

As will be described later in Examples, the *Aspergillus sojae* transformant transformed to overexpress the inserted genes is capable to produce selenoneine. Specifically, the *Aspergillus sojae* transformant can produce selenoneine by culturing in DPY medium suitable for the growth of the host *Aspergillus sojae* at 30° C. for 1 to 3 days to promote fungal cell growth, and then adding sodium selenite to this culture system and culturing at 37° C. for 3 to 5 days. The produced selenoneine is secreted outside the fungal cells or accumulated in the culture medium by lysis of fungal cells.

The ability to produce selenoneine of the transformant is not particularly limited. For example, when the transformant is cultured in DPY medium at 30° C. for 2 days, and then sodium selenite is added to this culture system and further cultured at 37° C. for 4 days, the production of selenoneine is 5 mg/l or more, preferably 10 mg/l or more, more preferably 15 mg/l or more, even more preferably 17 mg/l or more, and even more preferably 20 mg/l or more. The upper limit of selenoneine production when cultured in this manner is not limited and is typically around 100 mg/l.

As will be described later in Examples, the *Aspergillus sojae* transformant transformed to overexpress the inserted genes tends to have a greater ratio of selenoneine against the total amount of selenoneine and ergothioneine produced. Regarding the ability to produce selenoneine of the transformant, for example, when the transformant was incubated in DPY medium at 30° C. for 2 days, and when sodium selenite was added to this culture system and further incubated at 37° C. for 4 days, the ratio of the amount of selenoneine against the total amount of selenoneine and ergothioneine produced is 5% or more, more preferably 10% or more, even more preferably 20% or more, and still more preferably 40% or more. The upper limit of the above ratio when cultured in this manner is not particularly limited and is typically 100%. The upper limit of the above ratio when cultured in this manner is not particularly limited and is typically 100%.

The transformant may produce, along with the proteins produced by the inserted gene, wild-type proteins that have the same or different structural properties from the inserted gene proteins depending on the genes originally possessed by the host organism. Consequently, even if the transformant is not transformed with the inserted gene, the transformant may still be able to produce selenoneine.

(Method)

One embodiment of the method is a method for producing selenoneine including the step of applying histidine and a selenium compound to a transformant that has the inserted genes inserted therein and that can overexpress the inserted genes, to obtain selenoneine.

The method for applying histidine and a selenium compound to the transformant is not particularly limited and may be any method that can expose the transformant to histidine and the selenium compound to allow the activities or functions of inserted gene proteins to produce selenoneine. For example, the transformant may be cultured in a medium containing histidine and selenium compound and optimized for the growth of the transformant under culture conditions suitable for the transformant so as to produce selenoneine. The culture method is not particularly limited; for example, the solid culture or liquid culture technique performed under aerated or non-aerated condition may be employed. The amount of the selenium compound added is not particularly limited as long as the growth of the transformant is not inhibited. For example, the selenium compound may be present at sufficiently low levels relative to the fungal cell concentration at the initial stage of culturing. Specifically, it is added at a concentration of 0 mM. When it is desired to obtain large amounts of selenoneine, the amount of the selenium compound added may be increased during the course of culture or as the fungal cell concentration increases. For example, additional amounts of the selenium compound at a concentration of 0.01 to 10 mM, preferably 0.1 to 5 mM, may be added to the culture medium 1 to 3 days after the start of culture.

The medium may be any standard medium designed for culturing host organism and may be either a synthetic or natural medium that contains a carbon source, a nitrogen source, inorganic materials, and other nutrients at an appropriate ratio. When the host organism is a microorganism of the genus *Aspergillus*, the DPY medium as described in Examples below may be used, although not particularly limited. It is preferred, however, that the medium contain, as a component, iron (II) required for the activation of the EgtA protein. While iron (II) may be added to the medium in the form of a compound, it may also be added as a mineral-containing material.

The selenium compound is not particularly limited as long as it contains selenium as a constituent element. For example, it may be an organic or inorganic selenium compound or a salt thereof. Examples of organic selenium compounds and salts thereof include selenocysteine, selenocystine, selenomethionine, Se-(methyl)seleno-L-cysteine, selenopeptides, selenoproteins and salts thereof and selenium yeast. Examples of inorganic selenium compounds and salts thereof include selenic acid, selenious acid, selenium chloride, selenium, selenides, selenium sulfide, dimethylselenium, selenophosphate, selenium dioxide and salts thereof. Alternatively, the selenium compound may be an organic material containing an organic or inorganic selenium compound or a salt thereof. Examples of such organic materials include, but are not limited to, bonito fish (processed products and dried bonito), mustard (powdered mustard, grain mustard and mustard paste), pork (kidney, liver, and raw meat), beef (kidney, raw meat), anglerfish (liver, raw meat), codfish (cod roe, raw meat), bluefin tuna (red meat, raw meat), flatfish (raw meat), bonito fish (those caught in the fall season, raw meat), snow crabs (raw meat), sunflower seeds (fried, flavored), horse mackerel (grilled), tilefish (raw meat), granular seasoning, yellow fin tuna (raw meat), albacore (raw meat), oyster (boiled), and other food products known to be a rich source of selenium. The selenium compound may be one of or a combination of two or more of these materials.

The transformant in which the inserted gene is inserted and which overexpress the inserted gene is suitable for producing selenoneine from selenic acid and selenate such as sodium selenite and potassium selenite. Selenic acid and selenate are more economical than organic selenium compounds such as selenocysteine and selenocystine. In addition, selenic acid and selenate are less cell sensitive than selenious acid and may have less adverse effects on selenoneine production. Therefore, selenic acid and selenate are preferred as the selenium compounds to be used.

The culture condition of the transformant may be any culture condition of the host organism commonly known to those skilled in the art. For example, when the host organism is a filamentous fungus, the initial pH of the medium may be conditioned to 5 to 10 and the culture temperature to 20 to 40° C., and the culture time may be properly selected and may vary from several hours to several days, preferably from 1 to 7 days, and more preferably from 2 to 4 days. The culture means is not particularly limited; for example, an aerated and agitated deep culture, a shake culture, a static culture or other suitable culture techniques may be employed with the culture condition preferably adjusted so that sufficient amounts of dissolved oxygen are present. One example of the culture medium and culture condition for culturing microorganisms of the genus *Aspergillus* is as follow: a DPY medium, described in the Examples below, is cultured by agitation or shaking at 30° C., 10-300 rpm for 1 to 3 days for the purpose of fungal cell growth and by agitation or shaking at 37° C., 10-300 rpm for 3 to 5 days for the purpose of selenoneine production.

The method for extracting selenoneine from the culture after completion of the culture is not particularly limited. The culture supernatant recovered from the culture by filtration, centrifugation, or the like may be used for extraction as is, or the culture supernatant concentrate, in which the recovered culture supernatant is dried and/or concentrated, may be used for extraction.

The solvent used for extraction may be any solvent that can dissolve selenoneine, including, for example, organic solvents, such as methanol, ethanol, isopropanol and acetone; water-containing organic solvents composed of these organic solvents and water mixed together; and water, warm water and hot water. After addition of the solvent into the culture supernatant or the culture supernatant concentrate, selenoneine is extracted while the fungal cells are triturated as necessary. The temperature of the extraction solvent may be set to from room temperature to 100° C.

In order to purify selenoneine, the resulting extract can be subjected to various purification processes including centrifugation, filtration, ultrafiltration, gel filtration, separation by solubility difference, solvent extraction, chromatography (adsorption chromatography, hydrophobic interaction chromatography, cation exchange chromatography, anion exchange chromatography, and reversed-phase chromatography), crystallization, active carbon treatment, membrane treatment, and other purification processes.

The qualitative or quantitative analysis technique of selenoneine may be conducted by, for example, LC-ICP-MS, LC-MS/MS, LC-MS or HPLC according to the condition described in WO2017/026173 or Yamashita et al. (THE JOURNAL OF BIOLOGICAL CHEMISTRY VOL. 285, NO. 24, pp. 18134-18138, Jun. 11, 2010, EXPERIMENTAL PROCEDURES", "Selenium Determination"). A person skilled in the art would properly select the conditions for the analysis; for example, the analysis may be performed using the conditions described in Examples below.

According to the method in one embodiment of the present invention, selenoneine can be obtained at high yields. In the method described in WO2017/026173 of Patent Document 2, selenoneine is obtained from the cultured cells. In comparison, in the method in one embodiment of the present invention, selenoneine can be obtained from the culture supernatant. In the method in one embodiment of the present invention, selenoneine may be obtained by extraction from the cultured cells properly according to the method described in WO2017/026173 of Patent Document 2.

In the method in one embodiment of the present invention, various other steps or manipulations may be performed before, after, or during the above-described step as long as the objectives of the present invention can be achieved.
(Applications of Selenoneine)

Having advantageous characteristics of being a functional biological material with various physiological activities, as well as being a heat-resistant, water-soluble material, the selenoneine obtained by the method or the transformant to serve as one embodiment of the present invention is useful as general food and beverage products, functional food and beverage products, food and beverage products with function claims, food and beverage products for specified health use, food and beverage products with nutrient function claims, food and beverage products with health function claims, food and beverage products for special uses, nutritional supplement food and beverage products, health-promoting food and beverage products, supplements, beauty food and beverage products, cosmetic products, pharmaceutical products, quasi-pharmaceutical products, animal feeds, and raw-materials for producing these products.

Specifically, selenoneine is known to have antioxidant activity that is 1,000 times as high as that of it's thio analog, ergothioneine. For this reason, selenoneine can be useful as a biological antioxidant that exhibits the ability to capture hydroxyl radicals, the ability to suppress autoxidation of the hem iron, and other antioxidant activities. Examples of specific products containing selenoneine include, but are not limited to, supplements that can substitute selenious acid and selenomethionine, prophylactic or therapeutic agents for cancers and lifestyle-related diseases such as ischemic heart diseases, and antidotes for methyl mercury.

The present invention will now be described in further detail with reference to the following Examples, which are not intended to limit the present invention. The present invention may take various forms to the extent that the objectives of the present invention are achieved.

EXAMPLES

Example 1: Preparation of EgtA Expression Cassette with AsEgtA Gene Inserted (1) Extraction of Chromosomal DNA of *Aspergillus sojae* NBRC4239 Strain In a 150 ml Erlenmeyer flask, 30 mL of a polypeptone-dextrin medium (1 (w/v) % polypeptone, 2 (w/v) % dextrin, 0.5 (w/v) % $KH_2PO_4$, 0.1 (w/v) % $NaNO_3$, 0.05 (w/v) % $MgSO_4·7H_2O$, 0.1 (w/v) % casamino acid; pH 6.0) was prepared with distilled water. The medium was inoculated with the conidia of *Aspergillus sojae* NBRC4239 strain and was subjected to shake culture overnight at 30° C. The fungal cells were collected from the resulting culture medium by filtration and were placed between sheets of paper towel to remove moisture. The fungal cells were then triturated using a liquid nitrogen-chilled mortar and pestle while being chilled in liquid nitrogen. Using DNeasy Plant Mini Kit (Qiagen), the chromosomal DNA was extracted from the resulting triturated cells.

(2) Preparation of Construct Plasmid

The following elements were integrated into plasmid pUC19 to make a plasmid for making a construct (construct plasmid): Ptef, a promoter sequence of translation elongation factor gene tef1 (a 748 bp upstream region of tef1 gene; SEQ ID NO: 9); Talp, a terminator sequence of alkaline protease gene alp (a 800 bp downstream region of alp gene; SEQ ID NO: 10); and pyrG, a transformation marker gene that compensates for the requirement for uridine (1838 bp including a 407 bp upstream region of pyrG gene, a 896 bp coding region and a 535 bp downstream region; SEQ ID NO: 11). Specifically, the construct plasmid was prepared in the following manner.

Ptef, Talp and pyrG were amplified by PCR. The PCR was performed according to the protocol provided with the enzyme using chromosomal DNA of *Aspergillus sojae* NBRC4239 strain obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. Primers used to amplify Ptef, Talp and pyrG are shown in Tables 1 to 3 below. Of the sequences shown in the tables, the sequences shown in lower case are added sequences that serve to connect the amplified fragments of Ptef, Talp and pyrG in this order and further connect them to pUC19. The amplified DNA fragments were separated in 1 (w/v) % agarose gel and purified using QIAquick Gel Extraction Kit (Qiagen).

TABLE 1

| Amplified target region | Ptef |
|---|---|
| Forward primer SEQ ID NO: 12 | Ptef1_-748R_pUC cggtacccggggatcTGTG GACCAGACAGGCGCCACTC |
| Reverse primer SEQ ID NO: 13 | Ptef1_-1R_Talp atgtactcctggtacTTTG AAGGTGGTGCGAACTTTGTAG |

TABLE 2

| Amplified target region | Talp |
|---|---|
| Forward primer SEQ ID NO: 14 | Talp_1F GTACCAGGAGTACATTG GAGAGTTCTAC |
| Reverse primer SEQ ID NO: 15 | Talp_800R CCGATCCAACCACCCGG CTATCG |

TABLE 3

| Amplified target region | pyrG |
|---|---|
| Forward primer SEQ ID NO: 16 | PyrG_-407_F_Talp gggtggttggatcggTTGGGCT TATTGCTATGTCCCTGAAAGG |
| Reverse primer SEQ ID NO: 17 | PyrG_1431R_pUC cgactctagaggatcCCGCACC TCAGAAGAAAAGGATGA | pUC19 used was pUC19 linearized Vector provided with In-Fusion HD Cloning Kit (Clontech). Using In-Fusion HD Cloning Kit described above, the amplified Ptef, Talp and pyrG were ligated into pUC19 at In-Fusion Cloning Site located in the multiple cloning site according to the protocols provided with the kit, to obtain a construct plasmid.

The resulting construct plasmid was used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in a LB liquid medium containing 50 µg/ml ampicillin. The culture medium was centrifuged to collect fungal cells. Using FastGene Plasmid Mini Kit (Nippon Genetics), plasmid DNA was extracted from the collected fungal cells according to the protocols provided with the kit.

(3) Preparation of Construct for Inserting Gene of Interest

A DNA construct consisting of gene of interest AsEgtA connected between Ptef and Talp of a construct plasmid was prepared as follows.

An inverse PCR was performed using the construct plasmid obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The inverse PCR was performed according to the protocol provided with the enzyme to obtain a vector fragment of the construct plasmid. Primers used are shown in Table 4 below. The amplified vector fragments were separated in 1 (w/v) % agarose gel and purified using QIAquick Gel Extraction Kit (Qiagen).

TABLE 4

| Amplified target region | Construct plasmid |
|---|---|
| Reverse primer SEQ ID NO: 18 | Ptef_-1R TTTGAAGGTGGTGCGAACTTTGTAG |
| Forward primer SEQ ID NO: 14 | Talp_1F (above described) GTACCAGGAGTACATTGGAGAGTTCTAC |

To amplify the gene AsEgtA (SEQ ID NO: 1) derived from *Aspergillus sojae*, a PCR was performed using the chromosomal DNA of *Aspergillus sojae* NBRC4239 strain obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The PCR was performed according to the protocol provided with the enzyme. Primers used to amplify AsEgtA are shown in Table 5 below. Of the sequences shown in the table, the sequences shown in lower case are added sequences that serve to connect to the construct plasmid (between Ptef and Talp). The amplified DNA fragments were separated in 1 (w/v) % agarose gel and purified using QIAquick Gel Extraction Kit (Qiagen).

TABLE 5

| Amplified target region | AsEgtA |
|---|---|
| Forward primer SEQ ID NO: 19 | EgtA_1F_Ptef cgcaccaccttcaaaATGTCA CCTTTGGCTCTCTCTCC |
| Reverse primer SEQ ID NO: 20 | EgtA_2_925R_Talp atgtactcctggtacCTAAAG ATCCCGCACCAGGCGT |

The vector fragments amplified as described above and AsEgtA were connected using In-Fusion HD Cloning Kit according to the protocol provided with the kit to obtain a DNA construct for inserting a gene of interest in which AsEgtA has been inserted. The so-obtained DNA construct consists of a DNA fragment derived from pUC19, a DNA fragment of Ptef, a DNA fragment of AsEgtA, a DNA fragment of Talp, a DNA fragment of pyrG and a DNA fragment derived from pUC19 that are connected in series in the direction from the 5' to the 3'. In other words, the DNA construct in which the sequence Ptef-AsEgtA-Talp-pyrG was inserted into the MCS of pUC19 was obtained.

The resulting DNA construct was used to transform competent cells ECOS Competent *E. coli* JM109 (Nippon Gene) in accordance with the manufacturer's instructions to obtain transformed *E. coli*.

The resulting transformed E. coli was then subjected to shake culture overnight at 37° C. in a LB liquid medium containing 50 µg/ml ampicillin. The culture medium was centrifuged to collect fungal cells. Using FastGene Plasmid Mini Kit (Nippon Genetics), the plasmid DNA was extracted from the collected fungal cells according to the protocols provided with the kit.

A PCR was performed using the construct plasmid obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain an amplified fragment of Ptef-AsEgtA-Talp-pyrG. Primers used are shown in Table 6 below. The amplified DNA fragments were separated in 1 (w/v) % agarose gel and purified using QIAquick Gel Extraction Kit (Qiagen).

TABLE 6

| Amplified target region | Ptef-AsEgtA-Talp-pyrG |
|---|---|
| Forward primer SEQ ID NO: 21 | Ptef_-748F TGTGGACCAGACAGGCGCCACTC |
| Reverse primer SEQ ID NO: 22 | PyrG_1431R CCGCACCTCAGAAGAAAAGGATGA |

To amplify the Region 1 (Region 1 for homologous recombination) and Region 2 (Region 2 for homologous recombination) for homologous recombination to *Aspergillus sojae*, a PCR was performed using the chromosomal DNA of *Aspergillus sojae* NBRC4239 strain obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme. Primers used to amplify the Region 1 and Region 2 for homologous recombination are shown in Tables 7 and 8 below. Of the sequences shown in the tables, the sequences shown in lower case are added sequences that serve to connect pUC19, Ptef or pyrG. The amplified DNA fragments were purified using QIAquick PCR Purification Kit (Qiagen).

TABLE 7

| Amplified target region | Region 1 for homologous recombination |
|---|---|
| Forward primer SEQ ID NO: 23 | RT_-46F_pUC cggtacccggggatcGGTTGA AGCTGTCATTGTGTGCCGA |
| Reverse primer SEQ ID NO: 24 | RT1766R_Ptef cctgtctggtccacaAATCAG CTCCTCTGCGTGTTCTGC |

TABLE 8

| Amplified target region | Region 2 for homologous recombination |
|---|---|
| Forward primer SEQ ID NO: 25 | RT_1783F_PyrG tcttctgaggtgcggACGAA CTACAATGGTGCCTGGCTC |

TABLE 8-continued

| Amplified target region | Region 2 for homologous recombination |
|---|---|
| Reverse primer SEQ ID NO: 26 | RT_3667R_pUC cgactctagaggatcGCTTG GTAGAGTTGCCGCATCTGT |

The Region 1 for homologous recombination, Ptef-AsEgtA-Talp-pyrG and the Region 2 for homologous recombination obtained as described above and pUC19 linearized vector were connected using In-Fusion HD Cloning Kit according to the protocol provided with the kit to obtain a DNA construct in which the sequence of Region 1 for homologous recombination— Ptef-AsEgtA-Talp-pyrG-Region 2 for homologous recombination has been inserted into MCS of pUC19.

The resulting DNA construct was used to transform competent cells ECOS Competent E. coli JM109 (Nippon Gene) in accordance with the manufacturer's instructions to obtain transformed E. coli.

The resulting transformed E. coli was then subjected to shake culture overnight at 37° C. in a LB liquid medium containing 50 µg/ml ampicillin. The culture medium was centrifuged to collect fungal cells. Using FastGene Plasmid Mini Kit (Nippon Genetics), the plasmid DNA was extracted from the collected fungal cells according to the protocols provided with the kit.

To cleavage between Talp and pyrG in the construct plasmid obtained above, an inverse PCR was performed using the construct plasmid as a template DNA, Q5 Hot Start High-Fidelity 2× Master Mix (New England Biolabs) to serve as PCR enzyme, and T100 thermal cycler (BIO RAD) to serve as a PCR device. The inverse PCR was performed according to the protocol provided with the enzyme to obtain a vector fragment of the construct plasmid. Primers used are shown in Table 9 below. The amplified vector fragments were purified using QIAquick PCR Purification Kit (Qiagen).

TABLE 9

| Amplified target region | Construct plasmid |
|---|---|
| Reverse primer SEQ ID NO: 15 | Talp_800R(above described) CCGATCCAACCACCCGGCTATCG |
| Forward primer SEQ ID NO: 27 | PyrG_-407F TTGGGCTTATTGCTATGTCCCTGAAAGG |

To amplify the Region for looping out, a PCR was performed using the chromosomal DNA of *Aspergillus sojae* NBRC4239 strain obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme. Primers used to amplify the Region for looping out are shown in Table 10 below. Of the sequences shown in the table, the sequences shown in lower case are added sequences that serve to connect the construct plasmid (between Talp and pyrG). The amplified DNA fragments were purified using QIAquick PCR Purification Kit (Qiagen).

TABLE 10

| Amplified target region | Region for looping out |
|---|---|
| Forward primer SEQ ID NO: 28 | RT_3731F_Talp gggtggttggatcggACACCTAAGGCT CCTGAGAACGGT |
| Reverse primer SEQ ID NO: 29 | RT_4771R_PyrG_-407 tagcaataagcccaaAGATAAGCTCGG TTGCGAGGGAGT |

The vector fragment of construct plasmid obtained as described above and the Region for looping out were connected using In-Fusion HD Cloning Kit according to the protocol provided with the kit to obtain a DNA construct in which the sequence of Region 1 for homologous recombination— Ptef-AsEgtA-Talp- Region for looping out— pyrG-Region 2 for homologous recombination has been inserted into MCS of pUC19.

The resulting NDA construct was used to transform competent cells ECOS Competent E. coli JM109 (Nippon Gene) in accordance with the manufacturer's instructions to obtain transformed E. coli.

The resulting transformed E. coli was then subjected to shake culture overnight at 37° C. in a LB liquid medium containing 50 µg/ml ampicillin. The culture medium was centrifuged to collect fungal cells. Using FastGene Plasmid Mini Kit (Nippon Genetics), the plasmid DNA was extracted from the collected fungal cells according to the protocols provided with the kit.

A part of the Region 1 for homologous recombination in the resulting plasmid DNA was removed by the following procedure. Specifically, procedures from PCR to Self-ligation were performed using the construct plasmid obtained above to serve as a template DNA with KOD-Plus-Mutagenesis Kit (Toyobo) according to the protocols provided with the kit. T100 thermal cycler (BIO RAD) was used as a device. Primers used are shown in Table 11 below.

TABLE 11

| Amplified target region | Construct plasmid (Excluding a part of Region 1 for homologous recombination) |
|---|---|
| Forward primer SEQ ID NO: 30 | Ptef_-747F GTGGACCAGACAGGCGCCACTC |
| Reverse primer SEQ ID NO: 31 | RT_1233R_TaA TTATTGGGACGACCTGGGGTTAAGGGG |

The self-ligation reaction solution was used to transform competent cells ECOS Competent E. coli JM109 (Nippon Gene) in accordance with the manufacturer's instructions to obtain transformed E. coli.

The resulting transformed E. coli was then subjected to shake culture overnight at 37° C. in a LB liquid medium containing 50 µg/ml ampicillin. The culture medium was centrifuged to collect cells. Using FastGene Plasmid Mini Kit (Nippon Genetics), the plasmid DNA was extracted from the collected cells according to the protocols provided with the kit.

The nucleotide sequence of each DNA fragment inserted in the extracted plasmid DNA was determined to confirm that a DNA construct in which the sequence of Region 1 for homologous recombination (partially removed)— Ptef-AsEgtA-Talp-Region for looping out— pyrG-Region 2 for homologous recombination had been inserted was obtained.

As described above, a DNA construct in which the sequence of Region 1 for homologous recombination (partially removed)— Ptef-AsEgtA-Talp-Region for looping out— pyrG-Region 2 for homologous recombination has been inserted into MCS of pUC19 was obtained. The resulting plasmid for DNA construct was named pEgtA_s-LO_Py.

A PCR was performed using the construct plasmid obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain an EgtA expression cassette. Primers used are shown in Table 12 below. The amplified DNA fragments were s purified using QIAquick PCR Purification Kit (Qiagen).

TABLE 12

| Amplified target region | Region 1 for homologous recombination (partially removed)-Ptef-AsEgtA-Talp-Region for looping out-pyrG-Region 2 for homologous recombination |
|---|---|
| Forward primer SEQ ID NO: 32 | RT_33F CCATCCCACAAACACGGAGGAAACA |
| Reverse primer SEQ ID NO: 33 | RT_3649R ATCTGTTCTGGTCGGAGGTGTCTGAG |

As described above, an EgtA expression cassette in which the sequence of Region 1 for homologous recombination (partially removed)— Ptef-AsEgtA-Talp-Region for looping out— pyrG-Region 2 for homologous recombination has been included was obtained.

Example 2: Preparation of Aspergillus sojae Transformant with One Copy to Four Copies of EgtA Expression Cassette Introduced (1) Preparation of Aspergillus sojae KP-del Strain An Aspergillus sojae KP-del strain with disruption of pyrG gene and ku70 gene on the chromosome of an Aspergillus sojae NBRC4239 strain was prepared according to the description of Example 2 in the Patent No. JP6261039.

(2) Transformation of Aspergillus sojae KP-del Strain

In a 500 ml Erlenmeyer flask, conidia of the Aspergillus sojae KP-del strain were inoculated into 100 ml of a polypeptone dextrin liquid medium containing 20 mM uridine and the inoculated medium was subjected to shake culture at 30° C. for about 20 hours. Subsequently, the cells were collected. Protoplasts were prepared from the collected cells. The resulting protoplasts were then transformed with 20 µg of the EgtA expression cassette using the protoplast PEG technique and the transformants were incubated at 30° C. for 5 days or more in a Czapek-Dox minimal medium (Difco; pH 6) containing 0.5 (w/v) % agar and 1.2 M sorbitol to obtain the Aspergillus sojae transformant having the ability to form colonies.

Since pyrG, a gene that compensates for the requirement for uridine/uracil, had been introduced into the Aspergillus sojae transformant, the transformant was able to grow in the uridine/uracil-free medium and was selected as strains having the introduced target gene.

(3) Selection of *Aspergillus sojae* Transformant with One Copy of EgtA Expression Cassette There are eight sites on the chromosome of *Aspergillus sojae* where the EgtA expression cassette can be introduced by homologous recombination. A strain with one copy of the EgtA expression cassette at one of the sites was selected by PCR using the chromosomal DNA of the *Aspergillus sojae* transformant extracted according to Example 1 as a template. Primers used are shown in Table 13 below.

TABLE 13

| Amplified target region | Insertion region of EgtA expression cassette |
|---|---|
| Forward primer SEQ ID NOs: 34-41 | 5_261309F AAGACGTGGCAAACCACTCGCA RT4_-399F TTGGCTTGTTGGACCGTTGGTTGC 61_812749R TACCCAAACACCACATTCCCGCTC 36_1378060R AGCTTCCGAAACAATGGCGACGTG v3_18_121312R ACTGGTACGGATAACCCATGCAGCA 60_1595128R ATCACTACTCGTCGCAGGTGCAACAC v3_16_777681F AAGATGATCGACCTCCCAAGGTCCCA 46_5450F AGTACAGTTGGAGTCCCTCACAGG |
| Reverse primer SEQ ID NO: 42 | Ptef_-694R CCGGTCAAAACCCAAGCAGTTGTG |

The strain with an EgtA expression cassette introduced due to homologous recombination at one place was obtained. The EgtA expression cassette has been made to produce a PCR product using one combination among the eight combinations consisting of each of eight forward primers and one reverse primer.

(4) Preparation of pyrG-Removed Strain from which pyrG Marker has been Removed in EgtA Expression Cassette A region having the same sequence as the "Region for looping out" in the EgtA expression cassette is common to the downstream of the eight sites that can be introduced by homologous recombination. In the region where the EgtA expression cassette was introduced by homologous recombination, when homologous recombination occurs between the "Region for looping out" and the same sequence region downstream, the region comprising pyrG and Region 2 for homologous recombination is removed by looping out. Accordingly, a strain from which pyrG was removed from the introduced EgtA expression cassette was obtained by the following procedure.

A 5-FOA-resistant strain was obtained by inoculating and culturing the conidia of the strains obtained above, in which the EgtA expression cassette with one copy was introduced by homologous recombination, using 20 mM uracil-supplemented Czapek-Dox agar medium containing 3 mg/ml 5-fluorouracil (5-FOA). The overview of the step from the introduction of the EgtA expression cassette to the acquisition of the 5-FOA-resistant strain is shown in the following Scheme [V]. In the Scheme [V], "up" represents the Region 1 for homologous recombination, "down 1" represents the Region 2 for homologous recombination, and "down 2" represents the Region for looping out.

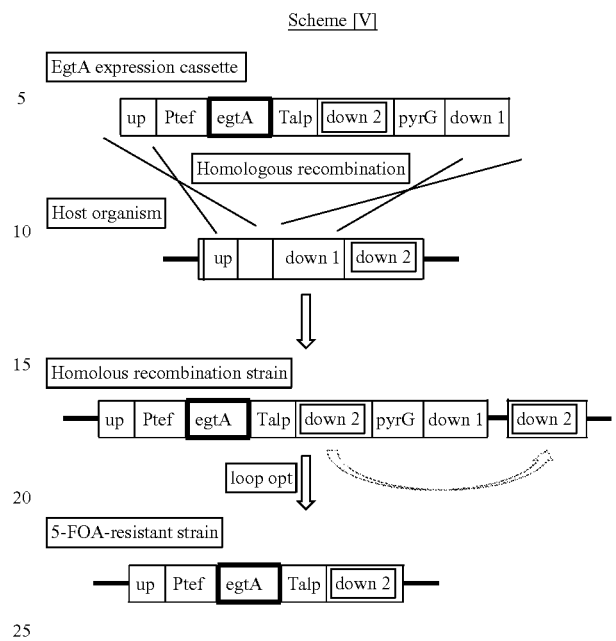

Scheme [V]

The resulting 5-FOA-resistant strain grew on 20 mM uracil-supplemented Czapek-Dox agar medium and not on uracil-free Czapek-Dox agar medium, i.e., confirmed to show the requirement for uracil.

The PCR was performed on the strain with confirmed the requirement for uracil, and it was confirmed that no pyrG-derived product was produced. Primers used are shown in Table 14 below.

TABLE 14

| Amplified target region | pyrG |
|---|---|
| Forward primer SEQ ID NO: 43 | pyrG_8F CCAAGTCGCAATTGACCTACAGCGCA |
| Reverse primer SEQ ID NO: 44 | pyrG_869R ATCCCATCCCTCTTTCTGGTACCGCT |

The PCR was performed using a pair of primers for selection of homologous recombinant strain as shown in Table 13, and it was confirmed that the combination of primers produced PCR products was the same in the strains before and after pyrG removal The resulting pyrG-removed strain was used below as a host for further introduction of the EgtA expression cassette.

(5) Preparation of *Aspergillus sojae* Transformants with Two Copies to Four Copies of EgtA Expression Cassette Introduced Strains with two copies, three copies and four copies of the EgtA expression cassettes were obtained by repeating the above steps (2) to (4); Transformation of the *Aspergillus sojae* host strain, Selection of an *Aspergillus sojae* transformant with the EgtA expression cassette and preparation of a pyrG-removed strain. The strains from which pyrG was removed by looping out were used as hosts for the next round. In addition, during the PCR for selection of homologous recombination strains, a strain in which the combination of primers producing products was newly increased by one set as compared with the host was selected.

Among the strain into which 4 copies of the EgtA expression cassette were introduced, the strain that retained pyrG before removing pyrG was designated as the sA4 strain.

Example 3: Preparation of *Aspergillus sojae* Transformant with EgtA, SatA and CysB Genes Introduced (1) Preparation of SatA Expression Cassette To amplify the gene SatA (SEQ ID NO: 2) derived from *Aspergillus sojae*, a PCR was performed using the chromosomal DNA of *Aspergillus sojae* NBRC4239 strain obtained in Example 1 to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme. Primers used to amplify SatA are shown in Table 15 below. Of the sequences shown in the table, the sequences shown in lower case are added sequences that serve to connect a vector fragment. The amplified DNA fragments were purified using QIAquick PCR Purification Kit (Qiagen).

TABLE 15

| Amplified target region | SatA |
|---|---|
| Forward primer SEQ ID NO: 45 | SatA_1F_Ptef cgcaccaccttcaaaATGGGATCTATAT ACGGCGTGGC |
| Reverse primer SEQ ID NO: 46 | SatA_1572R_Talp atgtactcctggtacTCAGCGCAAGAAT TTCTCTACTGCACC |

An inverse PCR was performed using the pEgtA_sLO_Py obtained in Example 1 to serve as a template DNA, Q5 Hot Start High-Fidelity 2× Master Mix (New England Biolabs) to serve as PCR enzyme, and T100 thermal cycler (BIO RAD) to serve as a PCR device. The inverse PCR was performed according to the protocol provided with the enzyme to obtain a vector fragment of the construct plasmid. Primers used are shown in Table 16 below. The amplified vector fragment was purified using QIAquick PCR Purification Kit (Qiagen).

TABLE 16

| Amplified target region | pEgtA _ sLO _ Py (Excluding AsEgtA) |
|---|---|
| Forward primer SEQ ID NO: 14 | Talp_1F(above described) GTACCAGGAGTACATTGGAGAGTTCTAC |
| Reverse primer SEQ ID NO: 18 | Ptef_-1R(above described) TTTGAAGGTGGTGCGAACTTTGTAG |

The vector fragment amplified as described above and SatA were connected using In-Fusion HD Cloning Kit according to the protocol provided with the kit to obtain a DNA construct in which the sequence of Region 1 for homologous recombination (partially removed)— Ptef-SatA-Talp-Region for looping out— pyrG-Region 2 for homologous recombination has been inserted into MCS of pUC19.

The resulting DNA construct was used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in a LB liquid medium containing 50 μg/ml ampicillin. The culture medium was centrifuged to collect cells. Using FastGene Plasmid Mini Kit (Nippon Genetics), the plasmid DNA was extracted from the collected cells according to the protocols provided with the kit.

The nucleotide sequence of each DNA fragment inserted in the extracted plasmid DNA was determined to confirm that a DNA construct in which the sequence of Region 1 for homologous recombination (partially removed)— Ptef-SatA-Talp-Region for looping out— pyrG-Region 2 for homologous recombination had been inserted was obtained.

The resulting DNA construct was named pSatA_sLO_Py.

(2) Bisection of SatA Expression Cassette

A PCR was performed using the pSatA_sLO_Py obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain two different vector fragments of the construct plasmid. Primers used are shown in Tables 17 and 18 below. The amplified vector fragments were purified using QIAquick PCR Purification Kit (Qiagen).

TABLE 17

| Amplified target region | pUC19(partial)-Region 1 for homologous recombination (partially removed)-Ptef-SatA-Talp |
|---|---|
| Forward primer SEQ ID NO: 47 | pUC19_2238F GTCAATACGGGATAATACCGCGCCAC |
| Reverse primer SEQ ID NO: 15 | Talp_800R(above described) CCGATCCAACCACCCGGCTATCG |

TABLE 18

| Amplified target region | Region for looping out-pyrG-Region 2 for homologous recombination-pUC19(partial) |
|---|---|
| Forward primer SEQ ID NO: 48 | RT_3731F ACACCTAAGGCTCCTGAGAACGGT |
| Reverse primer SEQ ID NO: 49 | pUC19_2252R TTATCCCGTATTGACGCCGGGCAAGA |

As described above, a DNA construct (SatA expression cassette 1) in which the sequence of pUC19 (partial)-Region 1 for homologous recombination (partially removed)— Ptef-SatA-Talp was inserted and a DNA construct (SatA expression cassette 2) in which the sequence of Region for looping out— pyrG-Region 2 for homologous recombination— pUC19 (partial) was inserted were obtained.

(3) Preparation of CysB Expression Cassette

To amplify the gene Pgpd (promoter) derived from *Aspergillus sojae*, the gene Tamy (terminator) and the gene CysB (SEQ ID NO: 3), a PCR was performed using the chromosomal DNA of *Aspergillus sojae* NBRC4239 strain obtained in Example 1 to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme. Primers used to amplify each gene are shown in Tables 19-21 below. Of the sequences shown in the tables, the sequences shown in lower case are added sequences that serve to connect to pUC19, Pgpd or Tamy. The amplified DNA fragments were purified using QIAquick PCR Purification Kit (Qiagen).

TABLE 19

| Amplified target region | Pgpd |
|---|---|
| Forward primer SEQ ID NO: 50 | Pgpd_-2000F_pUC cggtacccggggatcTTCACCGTATCTTAATAGAG AACGATCCGCAAC |
| Reverse primer SEQ ID NO: 51 | Pgpd_-1R TGTTTGGATGTGTCTGCTGGTGTGG |

TABLE 20

| Amplified target region | Tamy |
|---|---|
| Forward primer SEQ ID NO: 52 | Tamy_1F AGGGTGGAGAGTATATGATGGTACTGGT |
| Reverse primer SEQ ID NO: 53 | Tamy_803R_pUC cgactctagaggatcCCATGAGATACTATGA TATACTAAG |

TABLE 21

| Amplified target region | CysB |
|---|---|
| Forward primer SEQ ID NO: 54 | CysB_1F_Pgpd agacacatccaaacaATGTTCCGACA AAGTATTCGGCGCTTC |
| Reverse primer SEQ ID NO: 55 | CysB_1183R_Tamy tatactctccaccctTCAGGGGAGCA CGATGTACTTCTCCAAGT |

The Pgpd, Tamy and CysB obtained as described above and the pUC19 linearized Vector were connected using In-Fusion HD Cloning Kit according to the protocol provided with the kit to obtain a DNA construct in which the sequence of Pgpd-CysB-Tamy has been inserted into MCS of pUC19.

The resulting DNA construct was used to transform competent cells ECOS Competent E. coli JM109 (Nippon Gene) in accordance with the manufacturer's instructions to obtain transformed E. coli.

The resulting transformed E. coli was then subjected to shake culture overnight at 37° C. in a LB liquid medium containing 50 µg/ml ampicillin. The culture medium was centrifuged to collect cells. Using FastGene Plasmid Mini Kit (Nippon Genetics), the plasmid DNA was extracted from the collected cells according to the protocols provided with the kit.

The nucleotide sequence of each DNA fragment inserted in the extracted plasmid DNA was determined to confirm that a DNA construct in which the sequence of Pgpd-CysB-Tamy had been inserted was obtained.

A PCR was performed using the construct plasmid obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain the amplified fragments of Pgpd-CysB-Tamy. Primers used are shown in Table 22 below. Of the sequences shown in the table, the sequences shown in lower case are added sequences that serve to connect to the SatA expression cassette 1 and SatA expression cassette 2. The amplified DNA fragments were purified using QIAquick PCR Purification Kit (Qiagen).

TABLE 22

| Amplified target region | Pgpd-CysB-Tamy |
|---|---|
| Forward primer SEQ ID NO: 56 | Pgpd_-2000F_Talp gggtggttggatcggTTCACCGTATCTT AATAGAGAACGATCCGCA |
| Reverse primer SEQ ID NO: 57 | Tamy_803R_RT3745 aggagccttaggtgtCCATGAGATACTA TGATATACTAAGAT |

As described above, a CysB expression cassette in which the sequence of Pgpd-CysB-Tamy been inserted into was obtained.

(4) Preparation of SaCb Expression Cassette

The SatA expression cassette 1, the SatA expression cassette 2 and the CysB expression cassette obtained as described above were connected using In-Fusion HD Cloning Kit according to the protocol provided with the kit to obtain a DNA construct in which the sequence of Region 1 for homologous recombination (partially removed)— Ptef-SatA-Talp-Pgpd-CysB-Tamy-Region for looping out—pyrG-Region 2 for homologous recombination has been inserted into MCS of pUC19.

The resulting DNA construct was used to transform E. coli HST08 Premium Competent Cells (Takara Bio) in accordance with the manufacturer's instructions to obtain transformed E. coli.

The resulting transformed E. coli was then subjected to shake culture overnight at 37° C. in a LB liquid medium containing 50 µg/ml ampicillin. The culture medium was centrifuged to collect cells. Using QIAprep Spin Miniprep Kit (Qiagen), the plasmid DNA was extracted from the collected cells according to the protocols provided with the kit.

The nucleotide sequence of each DNA fragment inserted in the extracted plasmid DNA was determined to confirm that a DNA construct in which the sequence of Region 1 for homologous recombination (partially removed)— Ptef-SatA-Talp-Pgpd-CysB-Tamy-Region for looping out—pyrG-Region 2 for homologous recombination had been inserted was obtained.

The resulting DNA construct was named pSatA_CysB-_sLO_Py.

A PCR was performed using the construct plasmid obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain a SaCb expression cassette. In this case, the primers shown in Table 12 were used. The amplified DNA fragments were purified using QIAEX II Gel Extraction Kit (Qiagen).

As described above, a SaCb expression cassette in which the sequence of Region 1 for homologous recombination (partially removed)— Ptef-SatA-Talp-Pgpd-CysB-Tamy-Region for looping out-pyrG-Region 2 for homologous recombination been inserted into was obtained.

(5) Preparation of *Aspergillus sojae* Transformant with Four Copies of EgtA Expression Cassette and One Copy of SaCb Expression Cassette The strain obtained by removing pyrG from the sA4 strain prepared in Example 2 was transformed using the SaCb expression cassette. By selecting the transformant according to the method shown in the preparation of the EgtA expression cassette-introduced strain, a strain into which one copy of the SaCb expression cassette was further introduced by homologous recombination was obtained. The strain in which pyrG before looping out was retained was named SaCb strain.

Example 4: Preparation of *Aspergillus sojae* Transformant with EgtA and MetR Genes Introduced (1) Preparation of MetR Expression Cassette To amplify the gene MetR (SEQ ID NO: 4) derived from *Aspergillus sojae*, a PCR was performed using the chromosomal DNA of *Aspergillus sojae* NBRC4239 strain obtained in Example 1 to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme. Primers used to amplify MetR are shown in Table 23 below. Of the sequences shown in the table, the sequences shown in lower case are added sequences that serve to connect to a vector fragment. The amplified DNA fragments were purified using QIAquick PCR Purification Kit (Qiagen).

TABLE 23

| Amplified target region | MetR | |
|---|---|---|
| Forward primer SEQ ID NO: 58 | MetR_1F_Ptef | cgcaccaccttcaaaATGTCAGATG AGCACATCGCTCGTCA |
| Reverse primer SEQ ID NO: 59 | MetR_1561R_Talp | atgtactcctggtacCTAGTTATCG GTGCCCACACCCTTC |

An inverse PCR was performed using the pEgtA_sLO_Py obtained in Example 1 to serve as a template DNA, Q5 Hot Start High-Fidelity 2× Master Mix (New England Biolabs) to serve as PCR enzyme, and T100 thermal cycler (BIO RAD) to serve as a PCR device. The inverse PCR was performed according to the protocol provided with the enzyme to obtain a vector fragment of the construct plasmid. Primers used are shown in Table 16. The amplified vector fragments were purified using QIAquick PCR Purification Kit (Qiagen).

The vector fragment amplified as described above and MetR were connected using In-Fusion HD Cloning Kit according to the protocol provided with the kit to obtain a DNA construct in which the sequence of Region 1 for homologous recombination (partially removed)— Ptef-MetR-Talp-Region for looping out— pyrG-Region 2 for homologous recombination has been inserted into MCS of pUC19.

The resulting DNA construct was used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in a LB liquid medium containing 50 µg/ml ampicillin. The culture medium was centrifuged to collect cells. Using FastGene Plasmid Mini Kit (Nippon Genetics), the plasmid DNA was extracted from the collected cells according to the protocols provided with the kit.

The nucleotide sequence of each DNA fragment inserted in the extracted plasmid DNA was determined to confirm that a DNA construct in which the sequence of Region 1 for homologous recombination (partially removed)— Ptef-MetR-Talp-Region for looping out— pyrG-Region 2 for homologous recombination had been inserted was obtained.

The resulting DNA construct was named pMetR_sLO_Py.

A PCR was performed using the DNA construct obtained above to serve as a template DNA, Q5 Hot Start High-Fidelity 2× Master Mix (New England Biolabs) to serve as PCR enzyme, and T100 thermal cycler (BIO RAD) to serve as a PCR device. The PCR was performed according to the protocol provided with the enzyme to obtain a MetR expression cassette. In this case, the primers shown in Table 12 were used. The amplified DNA fragments were purified using QIAquick PCR Purification Kit (Qiagen).

As described above, a MetR expression cassette in which the sequence of Region 1 for homologous recombination (partially removed)— Ptef-MetR-Talp-Region for looping out— pyrG-Region 2 for homologous recombination been inserted into was obtained.

(2) Preparation of *Aspergillus sojae* Transformant with Four Copies of EgtA Expression Cassette and One Copy of MetR Expression Cassette The strain obtained by removing pyrG from the sA4 strain prepared in Example 2 was transformed using the MetR expression cassette. By selecting the transformant according to the method shown in the preparation of the EgtA expression cassette-introduced strain, a strain into which one copy of the MetR expression cassette was further introduced by homologous recombination was obtained. The strain in which pyrG before looping out was retained was named MetR strain.

Example 5: Preparation of *Aspergillus sojae* Transformant with EgtA, SatA, CysB and MetR Genes Introduced The strain obtained by removing pyrG from the SaCb strain prepared in Example 3 was transformed using the MetR expression cassette. By selecting the transformant according to the method shown in the preparation of the EgtA expression cassette-introduced strain, a strain into which one copy of the MetR expression cassette was further introduced by homologous recombination was obtained. The strain in which pyrG before looping out was retained was named SaCbMetR strain.

Example 6: Production of Selenoneine Using *Aspergillus sojae* Transformant

The *Aspergillus sojae* transformants prepared in Examples 2-5 were compared for their respective abilities to produce selenoneine in the following manner. The overview of the *Aspergillus sojae* transformants used is shown in the following table 24.

TABLE 24

| No. | Fungal strains | Transgene (numbers) |
|---|---|---|
| Example 2 | sA4 | EgtA (4) |
| Example 3 | SaCb | EgtA (4), SatA (1), CysB (1) |
| Example 4 | MetR | EgtA (4), MetR (1) |
| Example 5 | SaCbMetR | EgtA (4), SatA (1), CysB (1), MetR (1) |

In a 200 mL Erlenmeyer flask, conidia of each of the fungal strains were inoculated into 40 ml of a DPY liquid medium (0.5 (w/v) % histidine, 0.5 (w/v) % serine, 1 (w/v) % casein peptone, 2 (w/v) % dextrin, 0.5 (w/v) % yeast extract, 0.5 (w/v) % $KH_2PO_4$, 0.05 (w/v) % $MgCl_2 \cdot 6H_2O$; prepared with tap water; pH not adjusted) and the inoculated medium was subjected to shake culture at 160 rpm at 30° C. for 2 days. After the culture period, sodium selenite was added to the culture medium to reach a final concentration of 1 mM, and the culture was further subjected to shake culture at 160 rpm at 37° C. for 4 days.

After the culture period, the cell and the supernatant ware separated by filtration through a Kiriyama funnel (filter No. 3). The resulting supernatant was filtered through a 0.45 μm filter to obtain a supernatant fraction.

On the other hand, 8 ml water was added and agitated to suspend the fungal cells and form a cell suspension. The resulting cell suspension was subjected to a heat treatment at 100° C. for 15 min. Following the heat treatment, the suspension was centrifuged to collect the extracellular fluid as the supernatant, which in turn was filtered through a 0.45 μm filter to obtain a cell fraction extract.

Regarding the resulting extracts of the supernatant fraction and the cell fraction, selenoneine was quantified by LC-ICP-MS according to the conditions described in WO2017/026173 (Application No:PCT/JP2016/068128) and Yamashita et al. (THE JOURNAL OF BIOLOGICAL CHEMISTRY Vol. 285, No. 24, pp. 18134-18138, Jun. 11, 2010, "EXPERIMENTAL PROCEDURES", "Selenium Determination"). The total amount of Selenoneine and ergothioneine was subjected to HPLC analysis according to WO2017/026173 (Application No:PCT/JP2016/068128).

The results of measuring the amount of selenoneine are shown in FIGS. 1A and 1B, and the results of measuring the amount of ergothioneine are shown in FIG. 2. The results of calculating the ratio of the amount of selenoneine relative to the total amount of selenoneine and ergothioneine are shown in FIG. 3 according to the results of FIGS. 1A and 2.

As shown in FIGS. 1A and 1B, most of selenoneine was detected in the supernatant fraction regardless of which cell strains ware used. The SaCb, MetR and SaCbMetR strains all produced a larger amount of selenoneine than the sA4 strain. In the EgtA expression cassette-introduced strain, the production of selenoneine from sodium selenite could be enhanced by strengthening the selenocysteine synthesis system and the selenate assimilation system. Similarly, potassium selenite could also be used to produce selenoneine.

As shown in FIGS. 2 and 3, the SaCbMetR strain was found to produce selenoneine at high ratio. Although selenoneine and ergothioneine are difficult to isolate and purify due to their similar structures and molecular weights, these results indicated that the SaCbMetR strain can be used to obtain a high content of selenoneine by a process that simplifies the separation and purification of selenoneine.

Example 7: Toxicity of Selenium Compounds

The cytotoxicity of sodium selenite was tested as follows. To quantify cell proliferation, alamarBlue Cell Viability Reagent (Thermo Fisher Scientific) was used.

The mixture composed of 2× DPY liquid medium (2 (w/v) % polypeptone, 4 (w/v) % dextrin, 1 (w/v) % yeast extract, 1 (w/v) % $KH_2PO_4$, 0.1 (w/v) % $MgSO_4 \cdot 7H_2O$; pH not adjusted), 2× alamarBlue and $2 \times 10^4$ cells/ml the conidia of *Aspergillus sojae* NBRC4239 strain was dispensed in the volume of 100 μl into each well of a microplate. Similarly, 100 μl of an aqueous sodium selenite solution was added to each well so that the final concentration was 0 mM, 0.125 mM, 0.25 mM, 0.5 mM, 1 mM and 2 mM. The blank without the addition of the conidia and sodium selenite solution was used as a blank.

After incubating the microplate at 30° C. for 30 hours, absorbance at 570 nm was measured. A plot of the value calculated by subtracting absorbance at 600 nm of the blank from the measurement result according to the instruction manual of alamarBlue reagent is shown in FIG. 4.

As shown in FIG. 4, there was no growth inhibition by sodium selenite. No difference in the degree of mycelial growth was observed visually.

INDUSTRIAL APPLICABILITY

The method and the transformant in one embodiment of the present invention can be used to produce a large amount of selenoneine, which is said to have antioxidant activities and the ability to promote cell growth. Accordingly, the present invention is useful in the industrial-scale production of raw materials used to produce cosmetics and supplements with antioxidative activity.

The invention claimed is:

1. A method for producing selenoneine, comprising the step of applying histidine and a selenium compound to a transformant to obtain selenoneine, wherein the transformant has at least one gene selected from the group consisting of a SatA gene, a CysB gene and a MetR gene, and an EgtA gene inserted therein and can overexpress the inserted genes, and wherein the transformant is a microorganism of the genus *Aspergillus* selected from the group consisting of *Aspergillus sojae, Aspergillus oryzae, Aspergillus niger, Aspergillus tamarii, Aspergillus luchuensis, Aspergillus usamii, Aspergillus aculeatus* and *Aspergillus saitoi*.

2. The method according to claim 1, wherein the transformant has two copies to eight copies of the EgtA gene inserted therein and can overexpress the inserted copies of the EgtA gene.

3. The method according to claim 1, wherein the selenium compound comprises at least one selenium compound selected from the group consisting of selenic acid, selenious acid, selenium chloride, selenium tetrachloride, selenium, selenium dioxide, selenides, selenium sulfide, dimethylselenium, selenophosphate and salts thereof.

4. The method according to claim 1, wherein the host organism of the transformant is a microorganism expressing at least one enzyme selected from the group consisting of selenic acid reductase, selenocysteine lyase and serine dehydratase.

5. A transformant that has at least one gene selected from the group consisting of a SatA gene, a CysB gene and a MetR gene, and an EgtA gene inserted therein and can overexpress the inserted genes, wherein the transformant is a microorganism of the genus *Aspergillus* selected from the group consisting of *Aspergillus sojae, Aspergillus oryzae, Aspergillus niger, Aspergillus tamarii, Aspergillus luchuensis, Aspergillus usamii, Aspergillus aculeatus* and *Aspergillus saitoi*.

6. The transformant according to claim 5, wherein the transformant has two copies to eight copies of the EgtA gene inserted therein and can overexpress the inserted copies of the EgtA gene.

* * * * *